US012280174B2

(12) United States Patent
Garcia-Gareta et al.

(10) Patent No.: US 12,280,174 B2
(45) Date of Patent: Apr. 22, 2025

(54) EXTRACELLULAR MATRIX MATERIAL

(71) Applicant: Raft Enterprises Ltd., Middlesex (GB)

(72) Inventors: Elena Garcia-Gareta, Middlesex (GB); Nupur Kohli, Middlesex (GB)

(73) Assignee: Raft Enterprises Ltd.

( * ) Notice: Subject to any disclaimer, the term of this patent is extended or adjusted under 35 U.S.C. 154(b) by 185 days.

(21) Appl. No.: 16/333,558

(22) PCT Filed: Sep. 20, 2017

(86) PCT No.: PCT/GB2017/052796
§ 371 (c)(1),
(2) Date: Mar. 14, 2019

(87) PCT Pub. No.: WO2018/055361
PCT Pub. Date: Mar. 29, 2018

(65) Prior Publication Data
US 2019/0262502 A1 Aug. 29, 2019

(30) Foreign Application Priority Data
Sep. 20, 2016 (GB) .................................. 1615972.5

(51) Int. Cl.
*A61L 27/26* (2006.01)
*A61L 27/22* (2006.01)
*A61L 27/32* (2006.01)
*A61L 27/56* (2006.01)

(52) U.S. Cl.
CPC ............. *A61L 27/26* (2013.01); *A61L 27/225* (2013.01); *A61L 27/32* (2013.01); *A61L 27/56* (2013.01); *A61L 2430/02* (2013.01)

(58) Field of Classification Search
CPC ........ A61L 27/26; A61L 27/225; A61L 27/32; A61L 27/56; A61L 2430/02; A61L 27/46
See application file for complete search history.

(56) References Cited

U.S. PATENT DOCUMENTS

| 5,068,122 A | 11/1991 | Kokubo et al. |
| 2012/0219534 A1 | 8/2012 | Yayon et al. |

FOREIGN PATENT DOCUMENTS

| EP | 1532991 A1 | 5/2005 |
| IL | 154208 B | 5/2009 |
| JP | H08-117323 A | 5/1996 |
| JP | 2004-008634 A | 1/2004 |
| JP | 2015-515872 A | 6/2015 |
| KR | 20160072334 A | 6/2016 |
| WO | WO 2003/088925 | 10/2003 |
| WO | WO 2007/144644 | 12/2007 |
| WO | WO 2013/164635 | 11/2013 |
| WO | WO 2013/166566 | 11/2013 |
| WO | WO 2016/178174 | 11/2016 |

OTHER PUBLICATIONS

Chen et al., Acta Biomaterialia 8 (2012) 2297-2306. (Year: 2012).*
Edwards, et al.; "Characterization of cytolytic neutrophil activation in vitro by amorphous hydrated calcium phosphate as a model of biomaterial inflammation"; Journal of Biomedical Materials Research; vol. 96A, Issue 3, pp. 552-565 (Mar. 1, 2011).
Ahmed, et al.; "Fibrin: A Versatile Scaffold for Tissue Engineering Applications"; Tissue Engineering; vol. 14, No. 2, pp. 199-215 (2008).
Dong, et al.; "The mechanical and biological studies of calcium phosphate cement-fibrin glue for bone reconstruction of rabbit femoral defects"; International Journal of Nanomedicine; vol. 8, pp. 1317-1324 (2013).
Garcia-Gareta, et al.; "Comparison of mesenchymal stem cell proliferation and differentiation between biomimetic and electro-chemical coatings on different topographic surfaces"; Journal of Materials Science: Materials in Medicine; vol. 24, No. 1, pp. 199-210 (2013).
Garcia-Gareta, et al.; "Osteoinduction of bone grafting materials for bone repair and regeneration"; Bone; vol. 81, pp. 112-121 (2015).
Garcia-Gareta, et al.; "A Novel Multiparameter In Vitro Model of Three-Dimensional Cell Ingress Into Scaffolds for Dermal Reconstruction to Predict In Vivo Outcome"; BioResearch Open Access; vol. 2, No. 6, pp. 412-420 (Dec. 2013).
Habraken, et al.; "Calcium phosphates in biomedical applications: materials for the future?"; Materials Today; vol. 19, No. 2, pp. 69-87 (Mar. 216).
Hadjidakis, et al.; "Bone Remodeling"; Ann. N.Y. Acad. Sci.; vol. 1092, pp. 385-396 (2006).
Holt, et al.; "Viscoelastic Response of Human Skin to Low Magnitude Physiologically Relevant Shear"; J Biomed; vol. 41, No. 12, pp. 2689-2695 (Aug. 28, 2008).
Ignjatovic, et al.; "New biocomposite [biphasic calcium phosphate/poly-DL-lactide-co-glycolide/biostimulative agent] filler for reconstruction of bone tissue changed by osteoporosis"; Journal of Materials Science: Materials in Medicine; vol. 16, pp. 621-626 (2005).
Kokubo, et al.; "Solutions able to reproduce in vivo surface-structure changes in bioactive glass-ceramic A-W$^{3}$"; Journal of Biomedical Materials Research; vol. 24, pp. 721-734 (1990).
Legeros; "Calcium Phosphate-Based Osteoinductive Materials"; Chem. Rev.; vol. 108, pp. 4742-4753 (2008).
Lopez-Heredia, et al.; "Bulk physicochemical, interconnectivity, and mechanical properties of calcium phosphate cements-fibrin glue composites for bone substitute applications"; Journal of Biomedical Materials Research; vol. 101A, No. 2, pp. 478-490 (Feb. 2013).
Mishra, et al.; "Effect of Prevascularization on In Vivo Vascularization of Poly(Propylene fumarate)/Fibrin Scaffolds"; Biomaterials; vol. 77, pp. 255-266 (Jan. 2016).
Perez, et al.; "Utilizing Core-Shell Fibrous Collagen-Alginate Hydrogel Cell Delivery System for Bone Tissue Engineering"; Tissue Engineering; vol. 20, Nos. 1 & 2, pp. 103-114 (2014).
Qian, et al.; "Injectable calcium phosphate cement and fibrin sealant recombined human bone morphogenetic protein-2 composite in vertebroplasty: an animal study"; Bosn J Basic Med Sci; vol. 12, No. 4, pp. 231-235 (2012).

(Continued)

*Primary Examiner* — Robert S Cabral
(74) *Attorney, Agent, or Firm* — Mandar A. Joshi; Bozicevic, Field & Francis LLP

(57) ABSTRACT

An extracellular matrix material is described. The material has a cross-linked scaffold comprising fibrin or fibrinogen, and a bulking agent. Deposited on the scaffold is a calcium phosphate mineral phase. Also described are methods for forming such materials.

22 Claims, 23 Drawing Sheets

(56) References Cited

OTHER PUBLICATIONS

Saitoh, et al.; "Viscoelastic behavior of commercially available tissue conditioners under compression"; Dental Materials Journal; vol. 29, No. 4, pp. 461-468 (2010).
Sharma, et al.; "Albumin removal from human fibrinogen preparations for manufacturing human fibrin-based biomaterials"; Biochimie Open; vol. 1, pp. 6-10 (2015).
Sharma, et al.; "Method for estimating protein binding capacity of polymeric systems"; Biochimie Open; vol. 1, pp. 40-50 (2015).
Sharma, et al.; "Viscoelastic, physical, and bio-degradable properties of dermal scaffolds and related cell behavior"; Biomed. Mater; vol. 11, 12 pages (2016).
Wopenka, et al.; "A mineralogical perspective on the apatite in bone"; Materials Science and Engineering; vol. 25, pp. 131-143 (2005).
Xiu, et al.; "Different Angiogenic Abilities of Self-Setting Calcium Phosphate Cement Scaffolds Consisting of Different Proportions of Fibrin Glue"; BioMed Research International; vol. 2014; 9 pages (2014).

\* cited by examiner

EXTRACELLULAR MATRIX MATERIAL

CROSS-REFERENCE

This application is a national stage filing under 35 U.S.C. § 371 of PCT/GB2017/052796, filed Sep. 20, 2017, which claims the benefit of GB 1615972.5, filed Sep. 20, 2016, which applications are incorporated herein by reference in their entirety.

This invention concerns an extracellular matrix material, and methods for making such a material. The material may be used for promoting bone regeneration.

Regeneration of bone defects caused by trauma, infection, tumours or inherent genetic disorders is a clinical challenge. Regeneration of bone defects is also required in surgical procedures such as spinal fusions or hip and knee revision operations. Current surgical methods for treating bone defects often involve grafting of either autologous or allogenic bone. Autologous bone grafts are considered to be the "gold standard" for bone repair and regeneration. However, these methods are subject to limitations such as limited bone supply and donor site morbidity in the case of autologous bone graft or disease transmission and fracture and non-union in the case of allogenic bone grafting. These disadvantages are driving the development of new biomaterials that can act as efficacious bone graft substitutes (Garcia-Gareta et al. 2015).

Natural bone serves as the model for the development of bone graft substitutes. The different materials used to develop bone graft substitutes are: 1) natural and synthetic biodegradable polymers; 2) ceramics which include calcium-phosphate (CaP) materials and bioglasses; 3) metals; 4) carbon-based materials, such as carbon nanotubes and graphene; and 5) composites, which are a combination of two or more materials.

The biomineral present in bone is a highly substituted hydroxyapatite (Wopenka and Pasteris 2005; LeGeros 2008). Implants fabricated from it may interact with the surrounding bone tissue (Garcia-Gareta et al. 2015). Biomaterials incorporating CaP may be osteoconductive, meaning that they promote direct bonding with bone tissue on the biomaterial surface, and may be osteoinductive, which means that they induce the local stem cells to differentiate into bone cells (Garcia-Gareta et al. 2015).

Fibrin has been used in regeneration of tissues such as bone, cartilage, skin, tendons, ligaments, liver or cardiac tissue. However, for such applications, fibrin is typically in the form of a gel. For example, in the context of bone regeneration, combinations of fibrin glues and cements have been used to create injectable materials (Cui et al. 2010; Dong et al. 2013; Lopez-Heredia et al. 2013; Xiu et al. 2014). Fibrin has also been combined with synthetic polymers, such as poly(propylene fumarate) or poly-DL-lactide-co-glucolide to create composite bone graft substitutes (Mishra et al. 2016; Ignjatovic et al. 2005).

Although fibrin is a naturally occurring biodegradable polymer that shows excellent biocompatibility, pro-angiogenesis and bioactive properties, the mechanical and biodegradable properties of fibrin are very poor, therefore limiting its use (Ahmed et al. 2008).

So, there is a desire to provide improved bone regeneration compositions that overcome at least some of the aforementioned drawbacks.

According to the invention there is provided an extracellular matrix material comprising fibrin or fibrinogen; and a ceramic.

According to the invention there is provided an extracellular matrix material comprising fibrin or fibrinogen; a bulking agent and a ceramic.

The fibrin or fibrinogen, and optionally the bulking agent, may be cross-linked. Cross-linking may be achieved using methods described herein.

According to the invention, there is provided an extracellular matrix material comprising: a cross-linked scaffold comprising fibrin or fibrinogen, and a bulking agent; and a ceramic deposited on the scaffold.

According to the invention, there is provided an extracellular matrix material comprising a composite scaffold, the composite scaffold comprising fibrin and/or fibrinogen and a bulking agent, wherein the composite scaffold is cross-linked or has been stabilised by cross-linking, and wherein a ceramic is deposited on the composite scaffold.

Preferably, the ceramic is a calcium phosphate mineral phase.

According to the invention, there is provided an extracellular matrix material comprising: a cross-linked scaffold comprising fibrin or fibrinogen, and a bulking agent; and a calcium phosphate mineral phase deposited on the scaffold.

According to the invention, there is provided a method or process of preparing an extracellular matrix material, comprising: depositing a ceramic on to a cross-linked scaffold comprising fibrin or fibrinogen, and a bulking agent.

According to the invention, there is provided a method or process of preparing an extracellular matrix material, comprising: depositing a calcium phosphate mineral phase on a scaffold, wherein the scaffold comprises, or is formed from, fibrin or fibrinogen, and a bulking agent.

In a preferred embodiment, the scaffold comprises fibrin.

In some embodiments, the scaffold does not comprise fibres arranged in distinct layers.

According to the invention, the scaffold may be obtained, or is obtainable, by a process comprising: (a) mixing an aqueous solution of fibrinogen with a coagulating agent and a bulking agent; (b) incubating the mixture obtained in step (a) with a cross-linking agent; and (c) washing the cross-linked composition obtained in step (b) to remove the cross-linking agent.

The process of the invention may comprise: (a) mixing an aqueous solution of fibrinogen with a coagulating agent and a bulking agent; (b) incubating the mixture obtained in step (a) with a cross-linking agent; and (c) washing the cross-linked composition obtained in step (b) to remove the cross-linking agent.

In compositions used to form extracellular matrices of the invention (e.g. compositions for use in step (a) of the method of the invention, such as compositions comprising fibrinogen), the coagulating agent and the bulking agent (and optionally a foaming agent and/or stabilising agent), the fibrinogen may be present in an amount of 0.5 to 10%, by weight. Fibrinogen may be present as an aqueous solution buffered to a pH of between 4 and 10.

Fibrinogen may be buffered to a pH of between 7 and 8 (e.g. 7.4). Fibrinogen may be buffered with phosphate buffered saline (PBS) or HEPES buffered saline.

Porous, cross-linked fibrin scaffolds have been developed for the treatment of full thickness skin wounds. Such scaffolds are described in WO 2007/144644 A1 and WO 2013/164635 A1, a particular example of which is Smart Matrix®. Smart Matrix® is an intrinsically pro-angiogenic biomaterial which is a composite of fibrin with alginate, stabilised by glutaraldehyde cross-linking. The basic formulation to make the Smart Matrix® involves an enzymatic reaction between fibrinogen and thrombin, and alginate is used in order to provide bulking and support to the scaffold.

Surprisingly, the applicant has found that an extracellular matrix material of the invention may have a reduced degradation rate compared to such a scaffold without a deposited ceramic. This is particularly advantageous in the field of bone regeneration where it has been suggested that new bone formation in vivo may take up to four months (Hadjidakis and Androulakis 2006). Smart Matrix® has been observed in histological section up to about 5-6 weeks after implantation in a full-thickness skin wound in a porcine model.

In addition, despite the deposition of a ceramic such as a calcium phosphate mineral phase on the scaffold, the material of the invention may surprisingly maintain its porosity to allow cells, such as fibroblasts (e.g. dermal fibroblasts) and osteoprogenitor cells, to migrate and populate the biomaterial. The material may have good bio-compatibility, such that cells may grow, proliferate and differentiate effectively on the material, and yet the pro-angiogenic and bioactive properties of fibrin or fibrinogen may be maintained. The materials of the invention may thus maintain some of the beneficial properties provided by fibrin or fibrinogen, whilst overcoming some of the less favourable properties of fibrin and fibrinogen, such as its mechanical and biodegradable properties.

The term "calcium phosphate mineral phase" encompasses a mineral phase comprising calcium ions together with orthophosphates, metaphosphates or pyrophosphates and possibly hydrogen or hydroxide ions. For example, the calcium phosphate mineral phase may comprise monocalcium phosphate, dicalcium phosphate and/or tricalcium phosphate. In one example, the calcium phosphate mineral phase comprises an apatite such as hydroxyapatite. The ceramic may comprise octacalcium phosphate (OCP) and/or amorphous calcium phosphate (ACP). The ceramic may comprise a crystalline calcium phosphate mineral phase.

The ceramic may comprise a plurality, or combination, of different mineral phases, as described herein.

A calcium phosphate mineral phase may comprise one or more other elements, such as magnesium.

In some embodiments the calcium phosphate mineral phase does not comprise hydroxyapatite. In some embodiments, the calcium phosphate mineral phase may not comprise tricalcium phosphate, such as β-tricalcium phosphate.

The calcium phosphate mineral phase may be deposited on the scaffold using biomimetic deposition. For example, the scaffold may be contacted with, or immersed in, a fluid or solution. In one embodiment, the fluid may be a simulated body fluid (SBF) solution (Kokubo et al 1990). The fluid or solution may comprise calcium ions ($Ca^{2+}$) and phosphate ions, such as hydrogen phosphate ions ($HPO_4^{2-}$). The fluid or solution preferably further comprises sodium ions ($Na^{2+}$), potassium ions ($K^+$), magnesium ions ($Mg^{2+}$), chloride ions ($Cl^-$), hydrogen carbonate ions ($HCO_3^-$) and/or sulphate ions (mM $SO_4^{2-}$). The fluid or solution may comprise $Na^+$, $Ca^{2+}$, $HPO_4^{2-}$, $K^+·Mg^{2+}$, $Cl^-$, $HCO_3^-$ and $SO_4^{2-}$. The fluid or solution may comprise $Na^+$, $Ca^{2+}$, $HPO_4^{2-}$, $K^+·Mg^{2+}$, $Cl^-$ and $HCO_3^-$. The fluid or solution may comprise $Na^+$, $Ca^{2+}$, $HPO_4^{2-}$, $K^+·$ and $Cl^-$.

The fluid may comprise 1 to 30 mM $Ca^{2+}$. The fluid may comprise 1 to 20 mM $Ca^{2+}$. In some embodiments, the fluid may comprise 1 to 5 mM $Ca^{2+}$, for example, 2 to 3 mM $Ca^{2+}$, e.g. about 2.5 mM of $Ca^{2+}$. Alternatively, the fluid may comprise 10 to 30 mM $Ca^{2+}$, for example, 10 to 20 mM $Ca^{2+}$, e.g. 15 to 19 mM $Ca^{2+}$.

The fluid may comprise 0.5 to 10 mM $HPO_4^{2-}$. In some embodiments, the fluid may comprise 0.5 to 3 mM $HPO_4^{2-}$, for example 0.5 to 2 mM $HPO_4^{2-}$ e.g. about 1 mM of $HPO_4^{2-}$. Alternatively, the fluid may comprise 5 to 10 mM $HPO_4^{2-}$ e.g. 6 to 8 mM $HPO_4^{2-}$.

The fluid may comprise 100 to 800 mM $Na^+$. In some embodiments, the fluid may comprise 100 to 200 mM $Na^+$, for example 120 to 160 mM $Na^+$ or 140 to 150 mM of $Na^+$, e.g. about 142 mM $Na^+$. Alternatively, the fluid may comprise 500 to 800 mM $Na^+$, e.g. 600 to 800 mM $Na^+$.

The fluid may comprise 1 to 50 mM $K^+$. In some embodiments, the fluid may comprise 1 to 10 mM $K^+$, for example 3 to 7 mM $K^+$, e.g. about 5 mM of $K^+$. Alternatively, the fluid may comprise 10 to 40 mM $K^+$.

The fluid may comprise 0.5 to 20 mM $Mg^{2+}$. In some embodiments, the fluid may comprise 0.5 to 3 mM $Mg^{2+}$, for example 1 to 2 mM $Mg^{2+}$, e.g. about 1.5 mM of $Mg^{2+}$. Alternatively, the fluid may comprise 5 to 15 mM $Mg^{2+}$, e.g. 9 to 12 mM $Mg^{2+}$.

The fluid may comprise 100 to 800 mM $Cl^-$. In some embodiments, the fluid may comprise 100 to 200 mM $Cl^-$, for example 120 to 160 mM $Cl^-$. Preferably, the fluid comprises about 140 to 150 mM of $Cl^-$, e.g. about 148.8 mM $Cl^-$. Alternatively, the fluid may comprise 500 to 800 mM $Cl^-$, e.g. 600 to 800 mM C. The fluid may comprise 1 to 100 mM $HCO_3$. In some embodiments, the fluid may comprise 1 to 10 mM $HCO_3^-$, for example 2 to 8 mM $HCO_3^-$. Preferably, the fluid comprises 4 to 5 mM of $HCO_3^-$, e.g. about 4.2 mM $HCO_3^-$. Alternatively, the fluid may comprise 10 to 100 mM $HCO_3^-$, e.g. 20 to 80 mM $HCO_3^-$.

The fluid may comprise 1 to 10 mM $SO_4^{2-}$.

In one example, the fluid may comprise 1 to 30 mM $Ca^{2+}$, 0.5 to 10 mM $HPO_4^2$, 100 to 800 mM $Na^+$, 1 to 50 mM $K^+$, 0.5 to 20 mM $Mg^{2+}$, 100 to 800 mM $C^-$, 1 to 100 mM $HCO_3^-$, and 1 to 10 mM $SO_4^{2-}$.

In one example, the fluid may comprise 1 to 30 mM $Ca^{2+}$ 0.5 to 10 mM $HPO_4^{2-}$, 100 to 800 mM $Na^+$, 1 to 50 mM $K^+$, 0.5 to 20 mM $Mg^{2+}$, 100 to 800 mM $Cl^-$ and 1 to 100 mM $HCO_3^-$.

In one example, the fluid may comprise 1 to 30 mM $Ca^{2+}$ 0.5 to 10 mM $HPO_4^{2-}$, 100 to 800 mM $Na^+$, 1 to 50 mM $K^+$ and 100 to 800 mM $Cl^-$.

In one example, the fluid may comprise 1 to 5 mM $Ca^{2+}$ and 0.5 to 3 mM $HPO_4^2$, and optionally also comprise 100 to 200 mM $Na^+$, 1 to 10 mM $K^+$, 0.5 to 3 mM $Mg^{2+}$, 100 to 200 mM $Cl^-$ and 1 to 10 mM $HCO_3^-$.

In another example, the fluid may comprise 2 to 3 mM $Ca^{2+}$ and 0.5 to 2 mM $HPO_4^{2-}$ and optionally also comprise 120 to 160 mM $Na^+$, 3 to 7 mM $K^+$, 1 to 2 mM $Mg^{2+}$, 120 to 160 mM $Cl^-$ and 2 to 8 mM $HCO_3^-$.

In yet another example, the fluid may comprise about 2.5 mM $Ca^{2+}$ and about 1 mM $HPO_4^2$, and optionally also comprise about 142 mM $Na^+$, about 5 mM of $K^+$, about 1.5 mM of $Mg^{2+}$, about 149 mM $Na^+$ and about 4 mM $HCO_3^-$.

In one example, the fluid may comprise 10 to 30 mM $Ca^{2+}$, 5 to 10 mM $HPO_4^{2-}$, 500 to 800 mM $Na^+$, 10 to 40 mM $K^+$, 5 to 15 mM $Mg^{2+}$, 500 to 800 mM $Cl^-$, 10 to 100 mM $HCO_3^-$ and 1 to 10 mM $SO_4^{2-}$.

In one example, the fluid may comprise 10 to 30 mM $Ca^{2+}$, 5 to 10 mM $HPO_4^{2-}$, 500 to 800 mM $Na^+$, 10 to 40 mM $K^+$, 5 to 15 mM $Mg^{2+}$, 500 to 800 mM $Cl^-$ and 10 to 100 mM $HCO_3^-$.

In one example, the fluid may comprise 10 to 30 mM $Ca^{2+}$, 5 to 10 mM $HPO_4^{2-}$, 500 to 800 mM $Na^+$, 10 to 40 mM $K^+$ and 500 to 800 mM $Cl^-$.

Scaffolds may be immersed in or contacted with the fluid. Preferably, the scaffolds are immersed in the fluid. Scaffolds may be immersed in, or contacted with, the fluid for at least 12 hours, at least 1 day, at least 5 days, at least 6 days or at least 9 days. Scaffolds may be immersed in, or contacted with the fluid, for up to 10 days, preferably up to 9 days. For example, scaffolds may be immersed for 1 day to 10 days. Alternatively, scaffolds may be immersed in, or contacted with, the fluid for up to 48 hours (2 days). For example, scaffolds may be immersed in the fluid from 12 hours to 48 hours.

Immersion in, or contact with, the fluid may occur at 20 and 50° C., preferably 30 to 40° C., more preferably at about 37° C.

Preferably, the ceramic, such as the calcium phosphate mineral phase, is deposited throughout the scaffold. Preferably, the ceramic is deposited substantially evenly or uniformly on, or throughout, the scaffold. Even or uniform distribution may be assisted by a biomimetic method as described herein, for example by immersing the scaffold in a SBF fluid or solution.

Other methods of synthesising a calcium phosphate mineral phase, such as hydroxyapatite, are known to the skilled person. For example, hydroxyapatite may be synthesised by wet chemical deposition. For example, a hydroxyapatite nanocrystal suspension can be prepared by the following reaction:

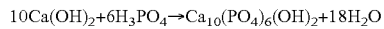

$$10Ca(OH)_2 + 6H_3PO_4 \rightarrow Ca_{10}(PO_4)_6(OH)_2 + 18H_2O$$

Alternatively, hydroxyapatite may be synthesised by a sol-gel method or by electrocrystallisation.

The calcium phosphate mineral phase may be in the form of globular mineral crystals and/or plate-like crystals deposited on the scaffold. These may be termed globular or plate-like morphologies. Examples of globular and plate-like morphologies are shown in FIG. 10. In some examples, the crystals may have an average (mean, mode or median) maximum linear dimension of 0.025 to 1 μm, preferably 0.05 to 0.8 μm.

The ceramic, such as the calcium phosphate mineral phase, may be at least 10%, at least 20%, at least 30%, at least 50%, by weight, of the extracellular matrix material of the invention. Preferably, the ceramic is at least 40%, by weight, of the extracellular matrix. More preferably, the ceramic is at least 50%, by weight, of the extracellular matrix.

The extracellular matrix material of the invention is preferably pre-formed or pre-fabricated, such that the matrix material is formed before it is applied or administered to a subject.

The extracellular matrix material of the invention is preferably sterile.

The extracellular matrix material of the invention may be contained within packaging, preferably sterile packaging, for storage prior to use.

Extracellular matrix materials of the invention may have particular rheological or viscoelastic properties. For example, the materials may have a shear or storage modulus (G'), at 20° C., of 50 to 100 kPa, for example 50 to 750 kPa, such as 50 to 600 kPa. G' may be at least 50 kPa. G' may be up to 1000 kPa. G' may be at least 200 kPa, or at least 400 kPa.

References herein to fibrinogen may include human fibrinogen. Alternatively, the fibrinogen may be bovine fibrinogen. The fibrinogen may have been purified from plasma. References to purified fibrinogen include fibrinogen at a purity level of greater than one of 75%, 80%, 85%, 90%, 95%, 97% or 99%. Preferably the purity is greater than 80%, more preferably greater than 90%. The fibrinogen may have been synthesised recombinantly.

In addition to native or naturally-occurring fibrinogen, references herein to fibrinogen may also include derivatives of fibrinogen such as fragments of fibrinogen or analogues of fibrinogen. It will be appreciated that any fragment or analogue thereof should retain the angiogenic function of native or naturally-occurring fibrinogen. Examples of fragments of fibrinogen include truncated forms of fibrinogen, such as fibrin A, fibrin B, fibrin C, fibrin D, fibrin X and fibrin Y. In a further embodiment, the truncated form of fibrinogen is fibrin E. Examples of analogues of fibrinogen include a modified derivative of fibrinogen wherein one or more amino acid residues of the peptide have been substituted by other naturally occurring or synthetic amino acid residues and/or wherein one or more amino acid residues have been deleted from the peptide and/or wherein one or more amino acid residues have been added to the peptide. A fibrinogen analogue may have a sequence identity of at least 70%, at least 80%, preferably at least 90%, most preferably at least 95% of native or naturally occurring fibrinogen, such as human fibrinogen. It will be appreciated that references to fibrinogen may not extend to electroprocessed fibrinogen or a derivative thereof such as those described in US 2004/0229333.

In a preferred example, the extracellular matrix of the invention comprises fibrin that has been formed following cleavage of fibrinogen by thrombin. Cleavage of fibrinogen by thrombin forms fibrin monomers and the fibrin monomers are able to polymerise to form fibres. Any derivatives of fibrinogen that may be used in the present invention, such as in the processes of the present invention, thus preferably retain the ability to be cleaved by thrombin to form fibrin monomer derivatives that are able to polymerise to form fibers. References herein to fibrin may thus also include fibrin formed from derivatives of fibrin monomers, such as analogues of fibrin monomers that are able to polymerise to form fibrin. A fibrinogen monomer analogue may have a sequence identity of at least 70%, at least 80%, preferably at least 90%, most preferably at least 95% of native or naturally occurring fibrin monomers, such as human fibrin monomers.

For example, analogues of fibrinogen and fibrin monomers preferably retain the globular structure consisting of two globular nodules at each end (D domains) and one globular nodule in the middle (E domain). Analogues of fibrin monomers preferably retain the ability to interact via knob-hole interactions of the γ and β holes, cavities present in the γ and β chains of fibrin monomers, and their complementary binding peptides (knobs) that are exposed by the excision of fibrinopeptides A and B from fibrinogen, by thrombin. The knobs extend from the central E domain and the γ and β holes are in the D domains. Consequently, the E domain of one monomer is able to interact with the D domain of a neighbouring monomer.

The coagulating agent used in processes of the invention may comprise an enzymatic or non-enzymatic coagulating agent. In a preferred example, the enzymatic coagulating agent is thrombin (IUBMB Enzyme nomenclature EC3.4.21.5) or a thrombin mimetic. The presence of thrombin or a thrombin mimetic within the extracellular matrix assists with formation of a stable composition in the form of a gel.

In one example, the enzymatic coagulating agent is thrombin, such as human thrombin. Thrombin is a chymotrypsin family endopeptidase, with trypsin-like substrate specificity. Thrombin converts fibrinogen into fibrin by selectively cleaving Arg-Gly bonds in fibrinogen to release fibrinopeptides A and B.

Thrombin is also described as a fibrinogenase, thrombase, thrombofort, topical thrombin-C, tropostasin, activated blood-coagulation factor II, blood-coagulation factor IIa, factor IIa, E thrombin, β-thrombin, and γ-thrombin. Therefore, references to a thrombin mimetic includes any structurally and functionally related agents, analogues and all derivatives thereof which demonstrate these properties. Examples of such thrombin mimetics include: Batroxobin (synonyms: defibrase, reptilase; IUBMB nomenclature SOI.176); Crotalase (derived from *Crotalus adamanteus* venom; synonyms: defibrinzyme; IUBMB nomenclature SOI.177); Bothrombin (derived from Bothrops jararaca venom; IUBMB nomenclature SOI.179); Atroxin (derived from Bothrops atrox; IUBMB nomenclature U9G.05); Ancrod (derived from Agkistrodon controtix toxin; synonyms Arvin, Protac, Protein C activator; IUBMB nomenclature SOI.178); and Gabonase (derived from Bitis gabonica; IUBMB nomenclature S01.430).

A non-enzymatic coagulating agent may include protamine or hyaluronan.

The presence of a bulking agent in the formation of the extracellular matrix material of the invention may provide the advantage of initiating formation of the extracellular matrix and may synergistically control the micro structure of the resultant mixture.

Examples of bulking agents include: alginates; biopolymers including xanthan gum and scleroglucan; carboxymethylcellulose; carrageenans (e.g. galactose sulfate); galactomannans i.e. locust bean gum and guar gum flower; hetastarch; a differentially soluble inert micro-bead; glycosaminoglycans (GAG; e.g. chondroitin 6-sulfate, chondroitin 4-sulfate, heparin, heparin bulphate, keratan sulfate, dermatan sulfate, chitin, chitosan, dextran sulphate or hyaluronan) and locust bean gum refined extracts, such as lecithins and pectins.

The bulking agent is preferably alginate or derivatised alginate. For example, the bulking agent may be sodium alginate or sodium propylglycoalginate. The presence of alginate within the extracellular matrix composition induces a calcium-independent co-precipitation reaction which provides the advantage of assisting with formation of a stable composition in the form of a gel.

Alginates are salts of alginic acid, which is a polyuronide made up of a sequence of two hexuronic acid residues: β-D-mannuronic acid (or M-residue); and α-L-guluronic acid (or G-residue). α-L-Guluronic acid is formed from enzymic epimerisation of β-D-mannuronic acid. These monomers can appear in homopolymeric blocks of consecutive G-residues (G-blocks), consecutive M-residues (M-blocks), alternating M and G-residues (MG-blocks) or randomly organized blocks. The relative amount of each block type varies both with the origin of the alginate. Alternating blocks form the most flexible chains and are more soluble at lower pH than the other blocks. G-blocks are more suitable as they form stronger gels than M-rich chains on the addition of divalent cations, e.g. $Ca^{2+}$, $Ba^{2+}$, $Cu^{2+}$ etc. This is because two G-blocks of more than 6 residues can form stable cross-linked junctions with divalent cations leading to a three-dimensional gel network (Simpson-N E, et al, Biomaterials 25 (2004) 2603-2610)

Alternatively, the bulking agent may be a glycosaminoglycan (GAG; e.g. chondroitin 6-sulfate, chondroitin 4-sulfate, heparin, heparin sulphate, keratan sulfate, dermatan sulfate, chitin, chitosan, dextran sulphate or hyaluronan).

The presence of a GAG within the composition may provide the advantage of stability enhancement by virtue of possessing amino acid residues which may be covalently cross-linked to fibrinogen during cross-linking of fibrinogen.

The bulking agent may be selected from hydroxyethylstarch, ethyl cellulose, Xanthan gum and agarose.

The extracellular matrix material of the invention may comprise a cross-linked bulking agent, The cross-linked bulking agent may be cross-linked to the fibrin or fibrinogen.

The process for forming the scaffold may comprise mixing an aqueous solution of fibrinogen with a foaming agent. So, the process may comprise mixing an aqueous solution of fibrinogen with a coagulating agent, a bulking agent and a foaming agent (and optionally a stabilising agent).

Examples of a foaming agent include a surfactant, a block co-polymer surfactant such as a pluronic surfactant, detergent or the like. The presence of a foaming agent provides the benefit of creating an effective foam structure while being capable of being easily removed from the composition, for example, by dissolving in ethanol in the case of a surfactant or by reduction of the calcium ion concentration to dissolve out a calcium dependent bead gel in the case of a micro-bead. In a further embodiment, the foaming agent comprises a surfactant, a non-ionic detergent, a thermo-sensitive gelling surfactant, a poloxamer (such as Pluronic®, particularly F68 or F127) or a poloxamine (such as Tetronic®1307), a diphosphatydyl-glycerol type phospholipid or a mixture of an immiscible phase (e.g. isopentane) with the aqueous fibrinogen solution phase. In a preferred embodiment, the foaming agent preferably comprises a non-ionic surfactant, such as a pluronic surfactant, preferably selected from Pluronic F68 and F127. In a particularly preferred embodiment, the foaming agent comprises Pluronic F68.

The foaming agent may consist of or comprise one or more surfactant agent(s) from the class of sugar surfactants, more preferably from the class of sugar-acyl surfactants. If the foaming agent is from the class of sugar acyl surfactants, it may have an acyl chain length from $C_8$ to $C_{12}$. Sugar-acyl surfactants may be selected from the class of pyranoside (particularly glucopyranoside), maltoside, and acyl-sucrose surfactants. The sugar-acyl surfactants may be selected from the group consisting of OGP, ODM, DGP and DdGP, TGP, HGP, DMP, decyl sucrose (nDS), dodecylsucrose (nDdS). Preferably, the sugar-acyl surfactants comprise or consist of DMP, DdGP and/or ODM.

The foaming agent may comprise or consist of at least two, or at least three sugar surfactants.

The foaming agent may comprise a plurality of sugar surfactants and at least one pluronic surfactant. In a particularly preferred embodiment, the foaming agent comprises DMP, DdGP, ODM and Pluronic F68.

The process for forming the scaffold may additionally comprise mixing an aqueous solution of fibrinogen with a stabilising agent, such as a protein stabilising agent. So, the process of the invention may comprise mixing an aqueous solution of fibrinogen with a coagulating agent, a bulking agent, a stabilising agent and optionally a foaming agent. A suitable stabilising agent, is trehalose. Other suitable stabilising agents may include small carbohydrates, poly-ols, such as glycerol, sorbitol, glucose and sucrose trehalose and raffinose. A preferred stabiliser is trehalose. Preferably, trehalose is present in an amount of 10-11% wt. with respect to fibrinogen, and preferably in an amount of 4-7.5% wt. in the mixture comprising fibrinogen, coagulating agent, bulking agent (and optionally foaming agent and/or stabilising agent).

The process step of mixing the aqueous solution of fibrinogen with the coagulating agent and a bulking agent (and optionally a foaming agent and/or stabilising agent) may alternatively or additionally comprise a casting, phase separation casting, foaming, lyophilising, extrusion, textiling, felting, spray coating or rapid manufacture step. In one embodiment, the mixture is cast, frozen and optionally lyophilised prior to the incubation step.

It will be appreciated that the casting step typically comprises procedures known to those skilled in the art of preparing extracellular matrix compositions. Typically, the casting step comprises incubation of the mixture obtained in step (a) at 37° C. for 15 minutes. Alternatively, incubation may occur for at least 30 mins, or at least an hour. For example, incubation may occur at 37° C. for an hour.

The freezing step will typically comprise storage of the cast mixture obtained in step (a) at below 0° C. (e.g. from −200° C. to −70° C.) from between several hours to overnight. In one embodiment, the cast mixture obtained in step (a) is frozen at −20° C. for 1 hour followed by freezing at −70° C. overnight.

It will be appreciated that the lyophilisation step typically comprises procedures known to those skilled in the art of lyophilisation. For example, lyophilisation of the cast, frozen mixture obtained in step (a) will typically comprise lyophilisation from between overnight to several days (e.g. 24 h) at a suitable pressure (e.g. $10^{-2}$ mBar) and at a suitable temperature (e.g. −600° C.).

The process for preparing an extracellular matrix, according to the invention, may comprise a step of causing the mixture of the aqueous solution of fibrinogen, the coagulating agent, the bulking agent (and optionally the foaming agent and/or stabilising agent) to foam and coagulate. Foaming may be achieved by mixing with aeration. In a further embodiment, foaming is achieved using an aerator (e.g. for 30s). Foaming may be achieved by whisking or blending.

The cross-linking agent used in the process of the invention to form the extracellular matrix material of the invention may be any one of a number of cross-linking agents or cross-linking techniques commonly known to those skilled in the art, such as chemical, radiation and dehydrothermal methods.

References herein to "cross-linking" concern covalent cross-linking. Cross-linking therefore does not encompass the process by which fibrin monomers associate and polymerise following the cleavage of fibrinopeptides A and B from fibrinogen, using thrombin. Preferably, cross-linking is achieved non-enzymatically, using a chemical cross-linking agent.

Examples of suitable chemical cross-linking agents include: carbodiimide coupling agents such as N-(3-dimethylaminopropyl)-N'-ethylcarbodiimide (EDC); N-hydroxysuccinimide (NHS), azide coupling agents; diisocyanate cross-linking agents such as hexamethylene diisocyanate; epoxide cross-linking agents such as epi-chlorhydrin, glycidylethers and glycidylamines; and aldehyde cross-linking agents such as formaldehyde, glutaraldehyde and glyoxal.

The chemical cross linking agent may comprises N-(3-dimethylaminopropyl)-N'-ethylcarbodiimide (EDC) and/or N-hydroxysuccinimide (NHS).

The chemical cross linking agent may comprise aldehyde cross-linking agents such as formaldehyde, glutaraldehyde and glyoxal. Aldehyde cross-linking agents have the advantage of providing extracellular matrix compositions with improved biocompatibility. For example, we have shown herein that the presence of an aldehyde crosslinking agent enhances in vitro spreading (e.g. seeding of human endothelial cells or fibroblasts onto the matrix). In a further embodiment, the aldehyde cross-linking agent is glutaraldehyde. The use of glutaraldehyde as a cross-linking agent provides a surprising advantage of yielding an optimal cross-link density more rapidly than other aldehydes and is also capable of achieving a relatively high density of cross-linking. In a preferred example, the chemical cross-linking agent is glutaraldehyde.

When the cross-linking agent comprises glutaraldehyde or N-(3-dimethylaminopropyl)-N'-ethylcarbodiimide (EDC) and/or N-hydroxysuccinimide (NHS), the process according to the invention may additionally comprise the addition of a toxicity reducing agent (e.g. lysine or sodium borohydride).

In one example, if the bulking agent comprises alginate, the process of the invention may comprise an additional cross-linking step to cross link alginate to fibrinogen or fibrin. In a further example, the cross-linking agent comprises periodic acid. Such an additional cross-linking step is likely to enhance the stability of the resultant composition.

Incubation with the cross-linking agent may typically be performed from between 1 minute and 24 hours (e.g. 4 hours) at a suitable temperature (e.g. 20-50° C. or room temperature).

When the cross-linking agent comprises an aldehyde cross-linking agent, the, process may additionally comprise the addition of a reducing agent. The reducing agent may be added after incubation but before washing to remove the cross-linking agent.

The presence of the reducing agent is believed to stabilise the cross-linking process and surprisingly results in an extracellular matrix composition with enhanced biological efficacy. Furthermore, the presence of the reducing agent is likely to reduce the cytotoxic effects caused by the leaching of un-reduced cross-linking agent from the composition.

Examples of a suitable reducing agent include sodium borohydride or agents with similar carbonyl group reactivity. The reducing agent may typically be added in an amount of 0.1% w/w to 10% w/w (e.g. about 1% w/w). The reducing agent may be added in an amount of 0.1% w/v to 10% w/v (e.g. about 1% w/v).

The process according to the invention may comprise the addition of a divalent or multivalent metal ion such as calcium (e.g. calcium chloride). The presence of calcium provides one or more of the following beneficial properties: (i) activation step of thrombin; (ii) gelation step of bulking agents such as alginate; (iii) control of the fibrinogen coagulation reaction; (iv) stability of cross-linked fibrinogen, fibrin or derived fragment to proteolytic degradation. It will be appreciated that the concentration of calcium will be selected such that it is sufficiently high enough to gelate alginate and/or activate thrombin, however, not exceed an amount which is likely leach from the composition and have cytotoxic effects. In one embodiment, calcium is added in a final concentration of between 1 and 50 mM. In a further embodiment, calcium is added in a final concentration of approximately 50 mM.

The washing step of the process of the invention removes the residual chemical cross-linking agent (and reducing agent if present), which may leach out over several hours or days. The washing step also increases biocompatibility of the resultant extracellular matrix compositions after cross-linking.

The washing in step may be achieved using a suitable washing regime (e.g. 5×5 min washes) in a suitable buffer, such as PBS or a solvent, such as water, ethanol, methanol, propanol, isopropanol or a mixture thereof. The washing step may be accompanied by sonication. The presence of sonication in the form of ultrasound (e.g. 5×30 s bursts) further enhances the removal of the cross-linking agent (and reducing agent if present). The washing step may comprise 5×5 min washes in a mixture of ethanol/water (e.g. 95% v/v ethanol and 5% v/v water).

The extracellular matrix material of the invention may be frozen and optionally lyophilised prior to use.

The extracellular matrix material of the invention preferably has a distribution of pore sizes up to 400 µm. For example, the extracellular matrix material may have a majority of pores with a size in the range of 20-270 µm.

The extracellular matrix material of the invention preferably has bulk porosity above 50%, preferably above 60%, more preferably above 75%, such as above 80%.

According to a further aspect of the invention there is provided the extracellular matrix material as defined herein for use in treating bone defects, such as wounds or fractures, or for promoting bone regeneration.

According to a further aspect of the invention there is provided use of an extracellular matrix material as defined herein for use in the manufacture of a medicament for treating bone defects, such as wounds or fractures, or for promoting bone regeneration.

According to a yet further aspect of the invention there is provided a method of treating bone defects, such as wounds or fractures, which comprises application of an extracellular matrix material as defined herein, to the site of a bone defect.

The extracellular matrix material as hereinbefore described may be used for in vivo, in vitro or ex vivo bone regeneration.

Examples of the invention are now described by way of example only, with reference to the accompanying drawings, in which:

FIG. 1 shows SEM photos of Smart Matrix® at 150× and 40,000× magnifications showing its open, interconnected porosity and fibrous nature as well its micro-porosity (left) and nano-porosity (right), wherein the fibres are nano-sized mimicking the in vivo scenario where cells are in contact with a nano-sized extracellular matrix;

FIG. 2 shows SEM photos at 40,000× of calcium phosphate-Smart Matrix® (CaP-SM) showing mineral deposition over time after immersion in simulated body fluid (SBF): top left 2 days in SBF, top right 4 days in SBF, bottom left 6 days in SBF and bottom right 9 days in SBF;

FIG. 3 shows SEM photos at 150× of CaP-SM showing the reduction in micro-porosity after immersion in SBF: top left 2 days in SBF, top right 4 days in SBF, bottom left 6 days in SBF and bottom right 9 days in SBF;

Figure 6:
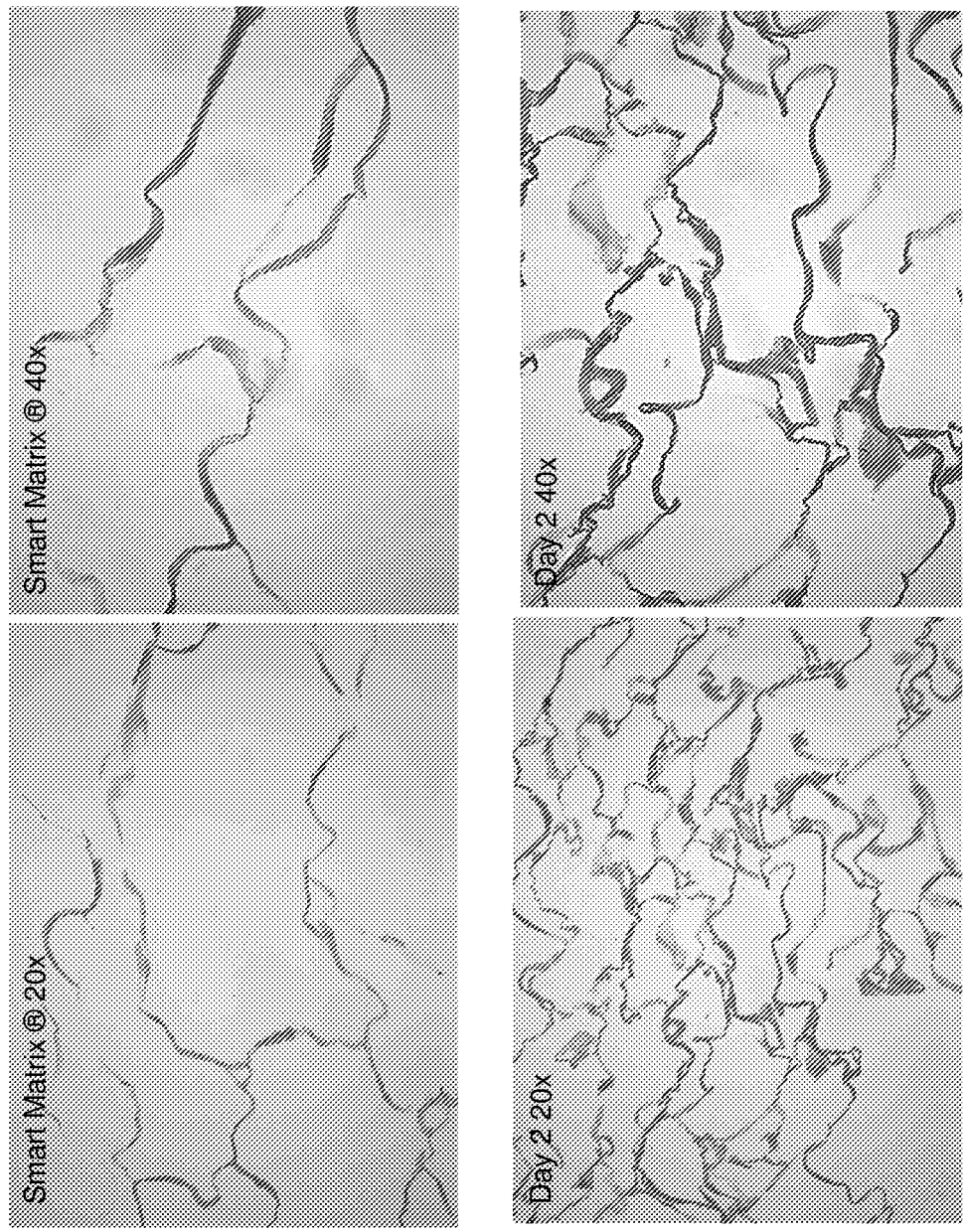
Figure 6:
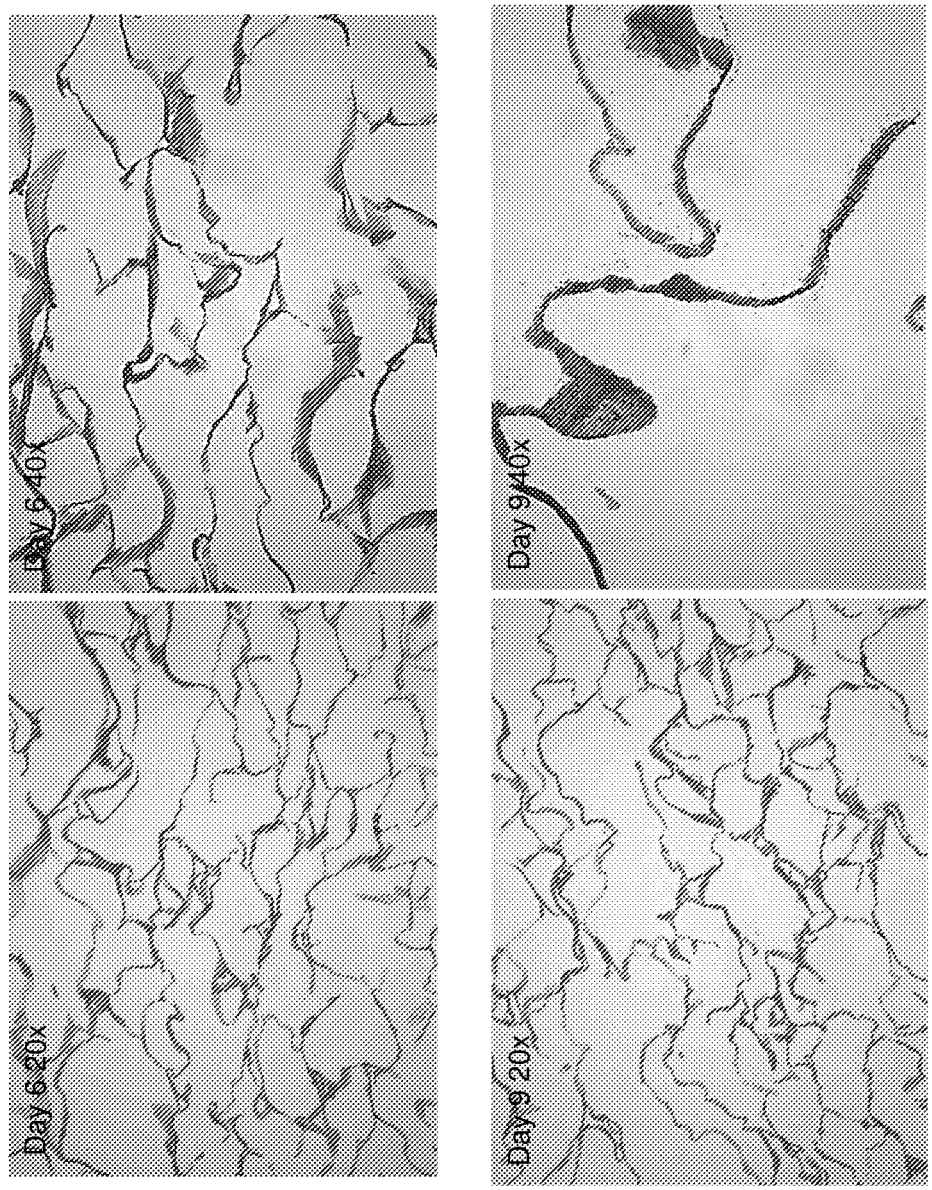
Figure 7:
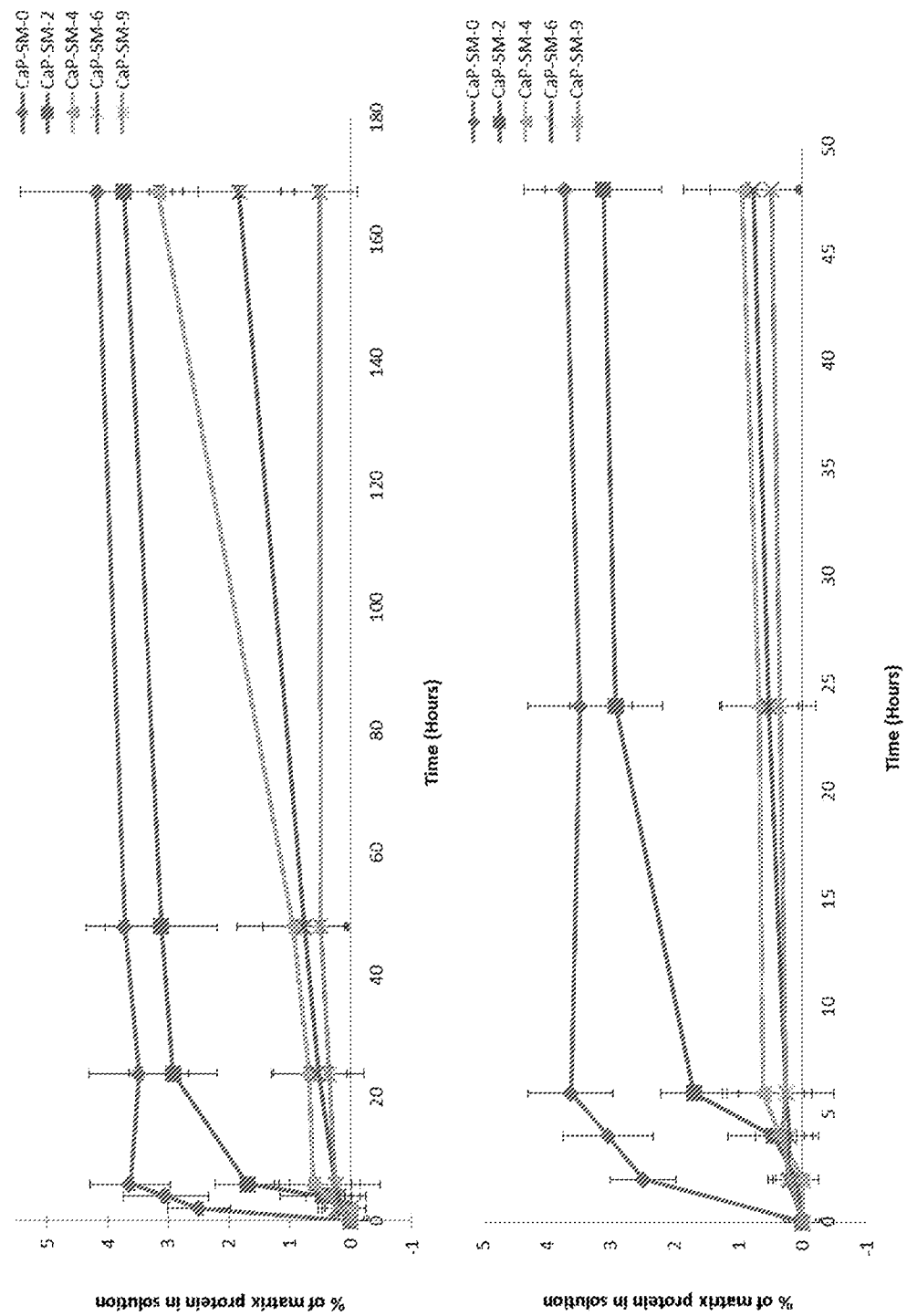

FIG. 6 shows Von Kossa staining results for control sample (Smart Matrix®), day 2 of immersion, day 6 of immersion and day 9 of immersion in SBF. Photos on the left are at 20× magnification and photos on the right are at 40× magnification;

FIG. 7 shows in vitro degradation of Smart Matrix® (CaP-SM 0) and CaP-SM immersed in SBF for different time periods. Top, results up to 7 days (168 h); bottom, close-up results that show the sharp decrease in the degradation rate in the first 6 h for the CaP-SM scaffolds compared to Smart Matrix®. Results show average±standard deviation.

Figure 8:
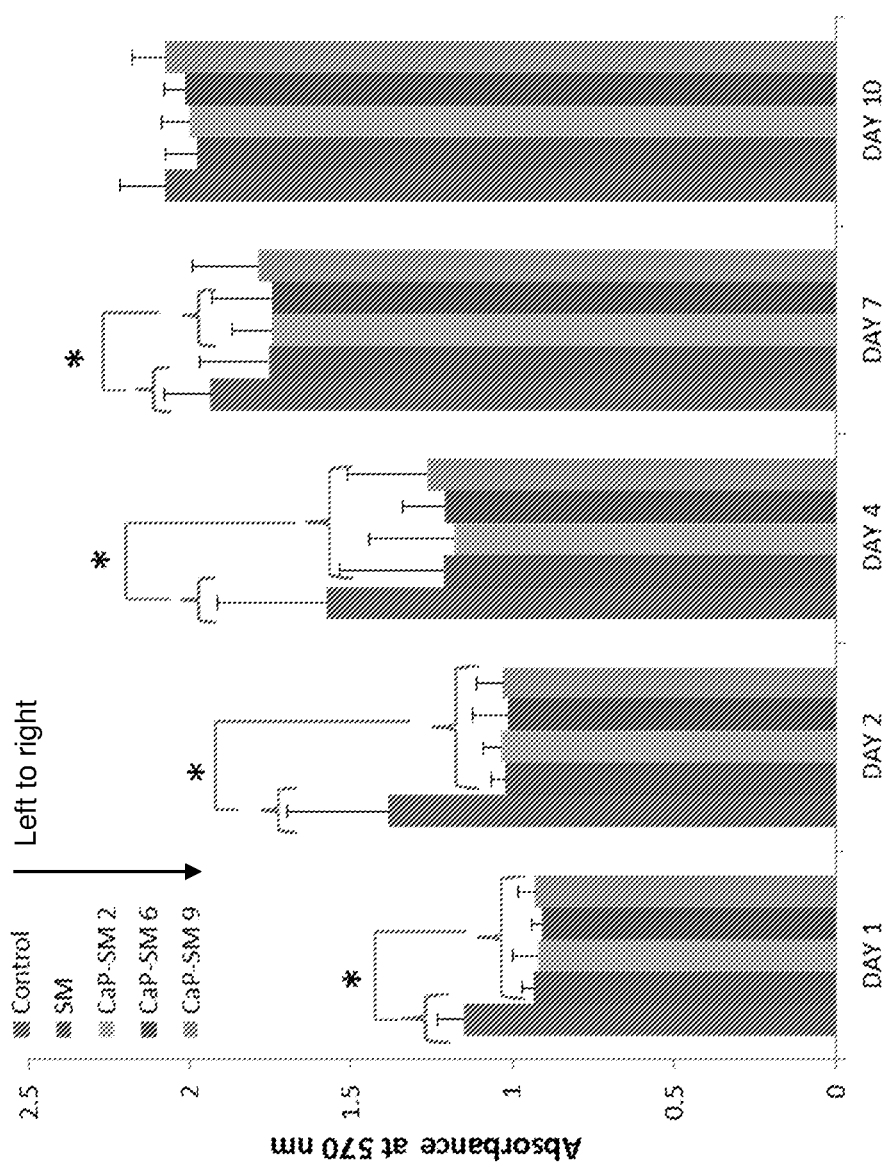
Figure 9:
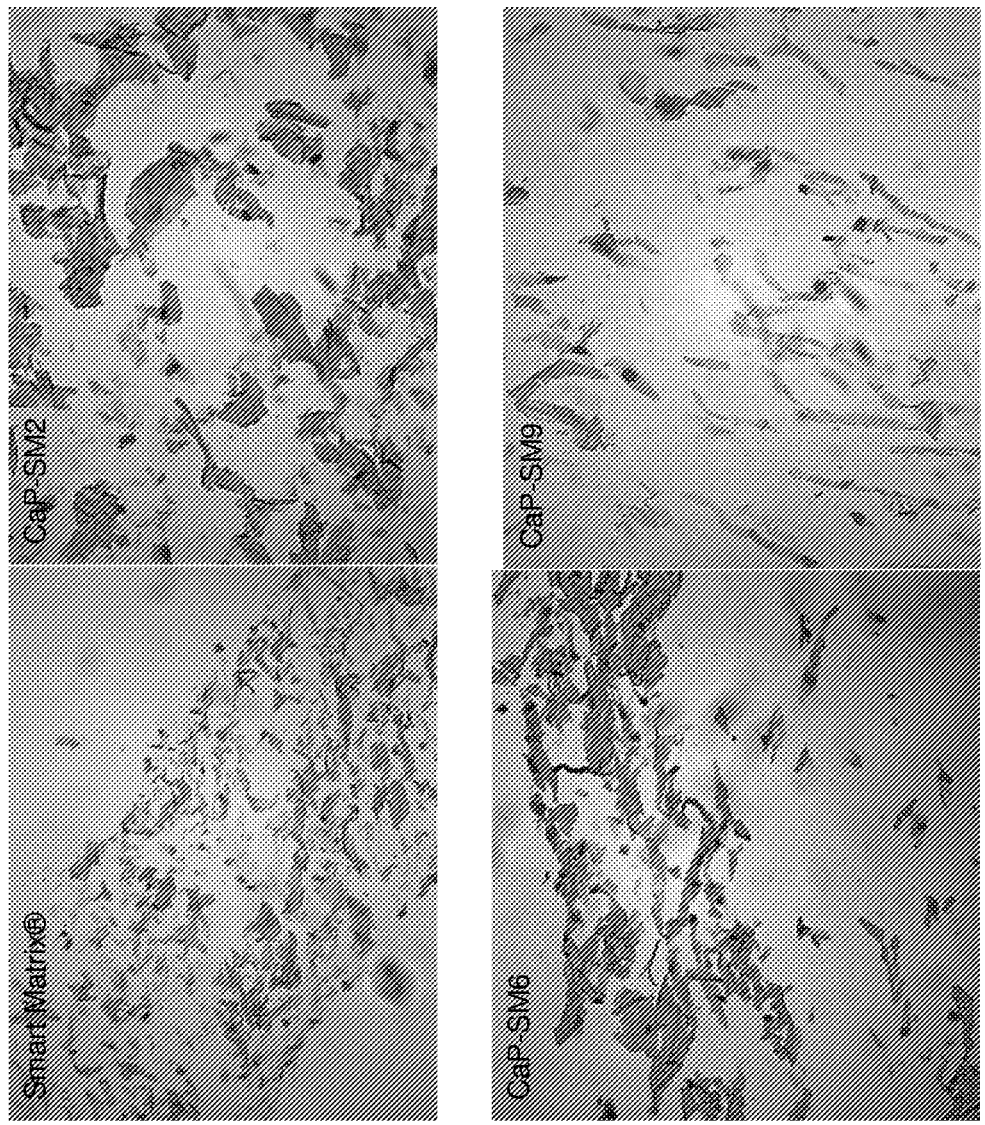
Figure 10:
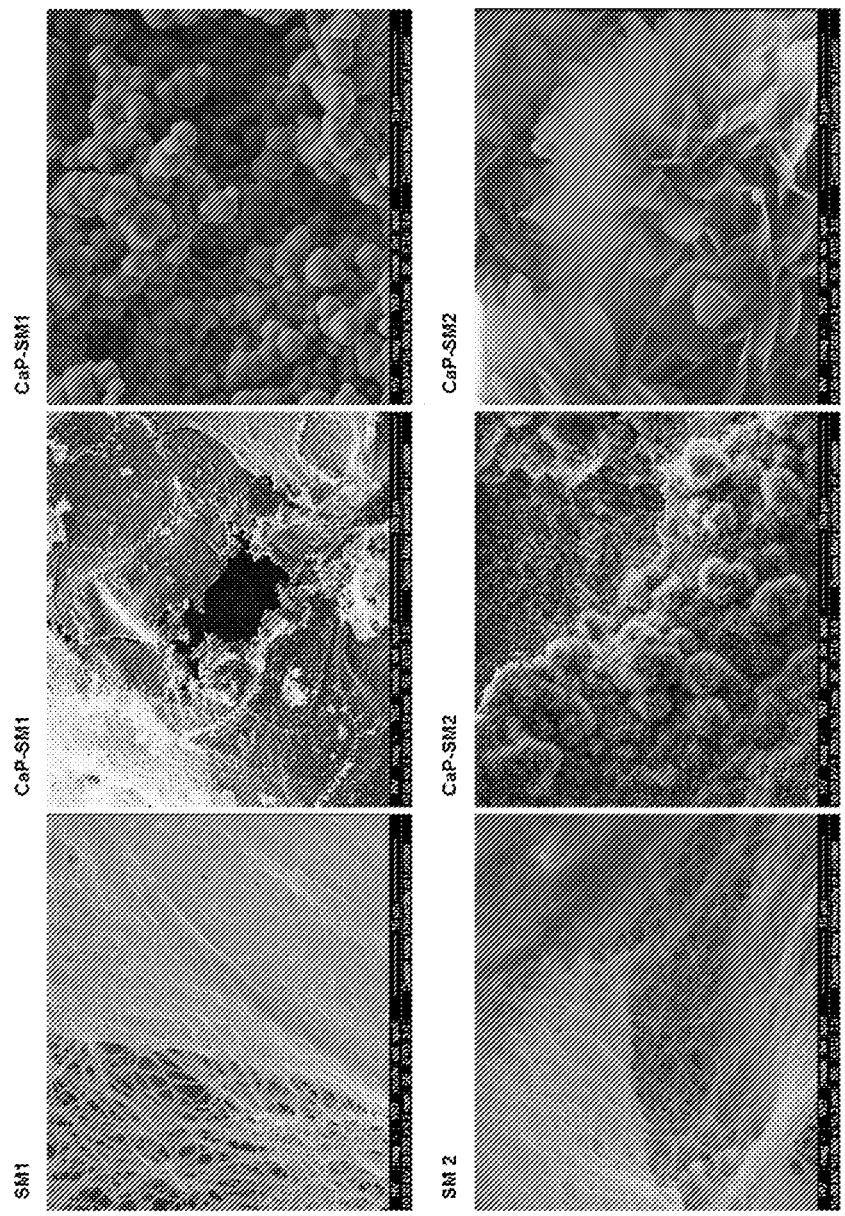
Figure 11:
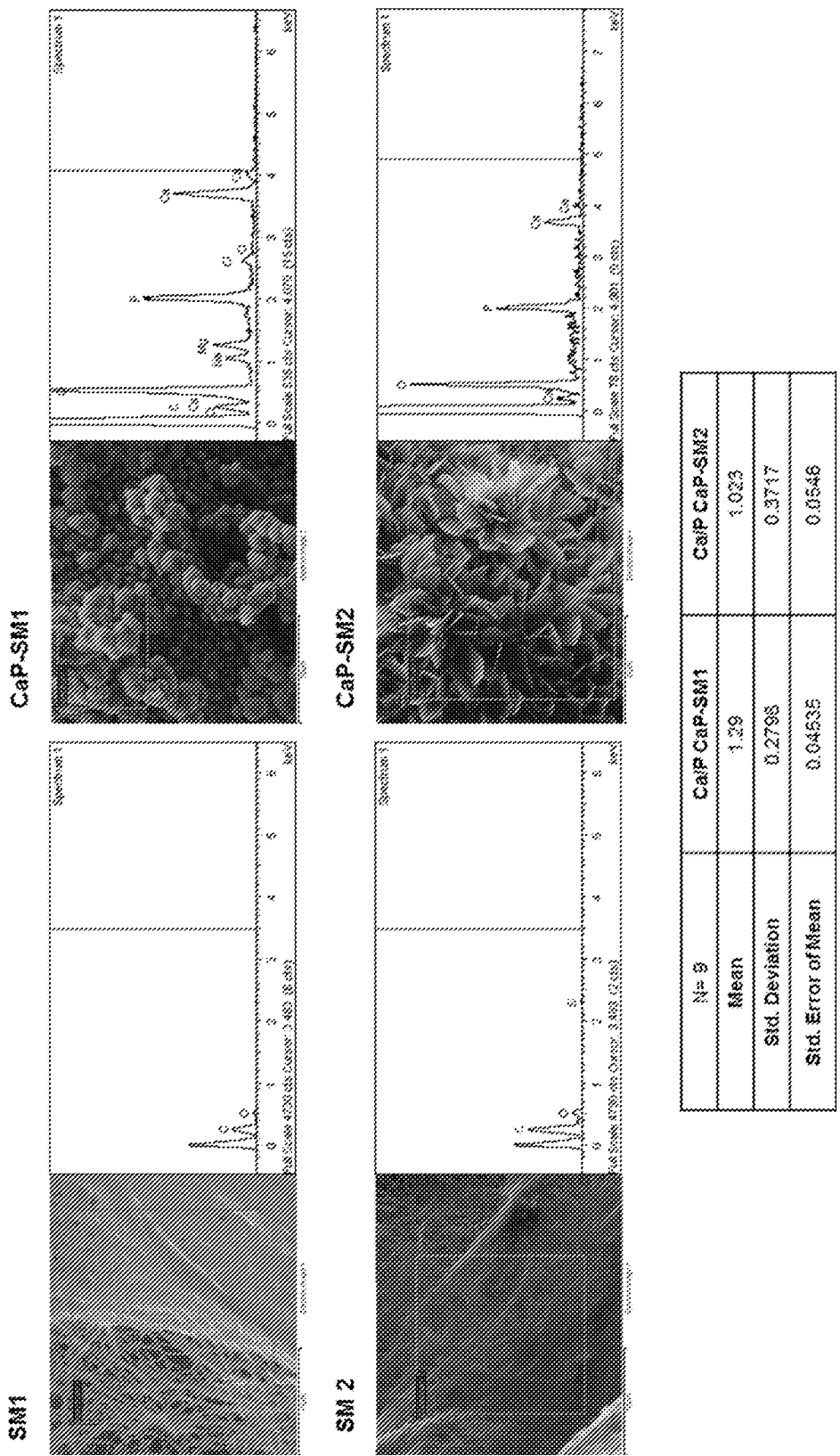
Figure 12:
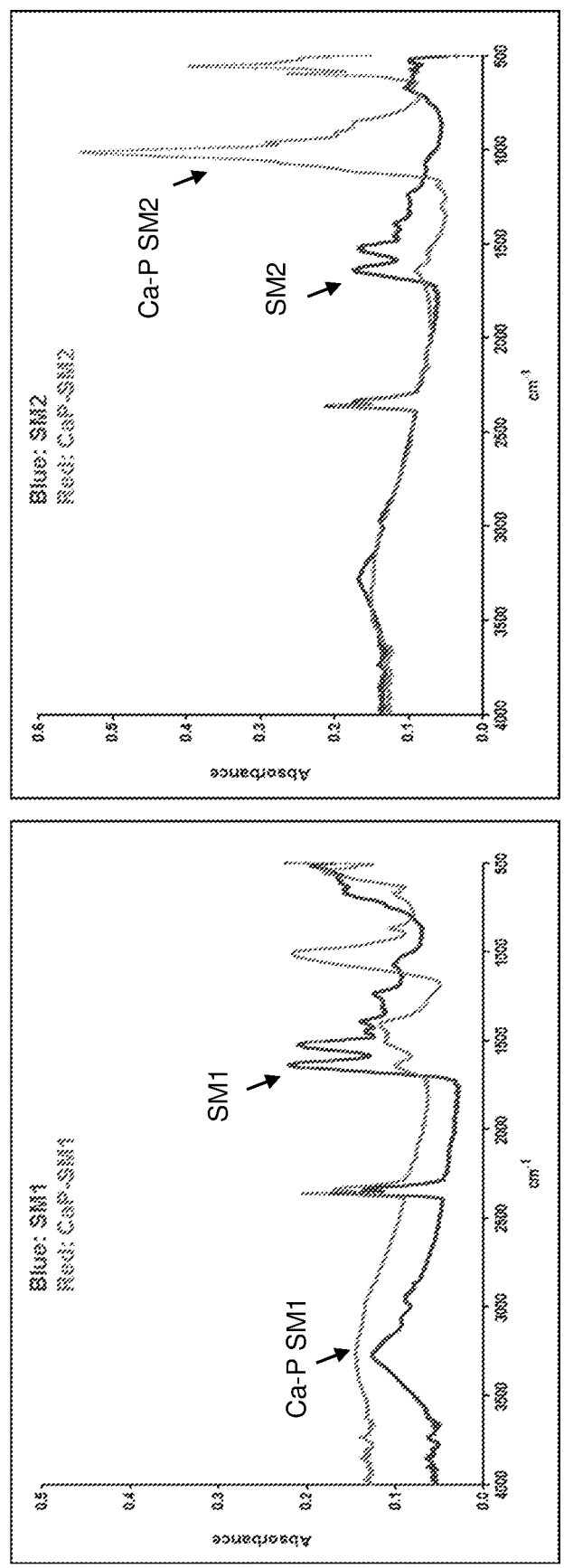
Figure 13:
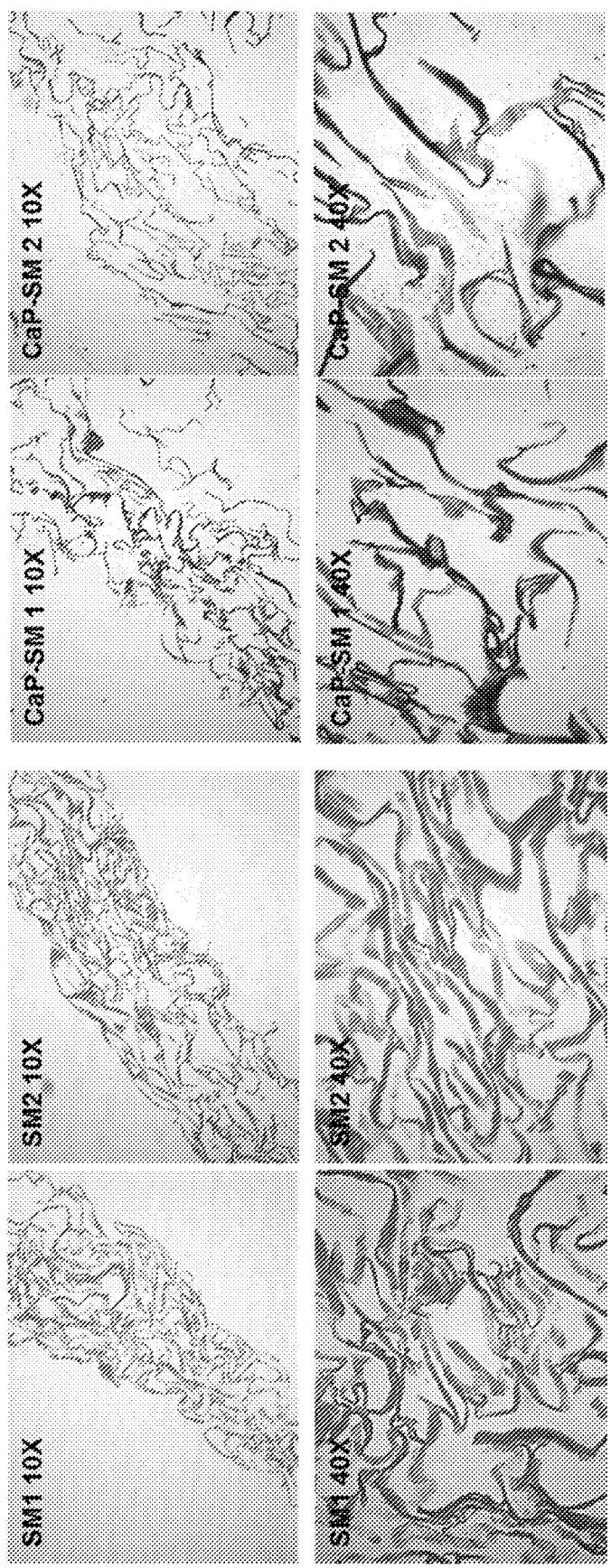
Figure 14:
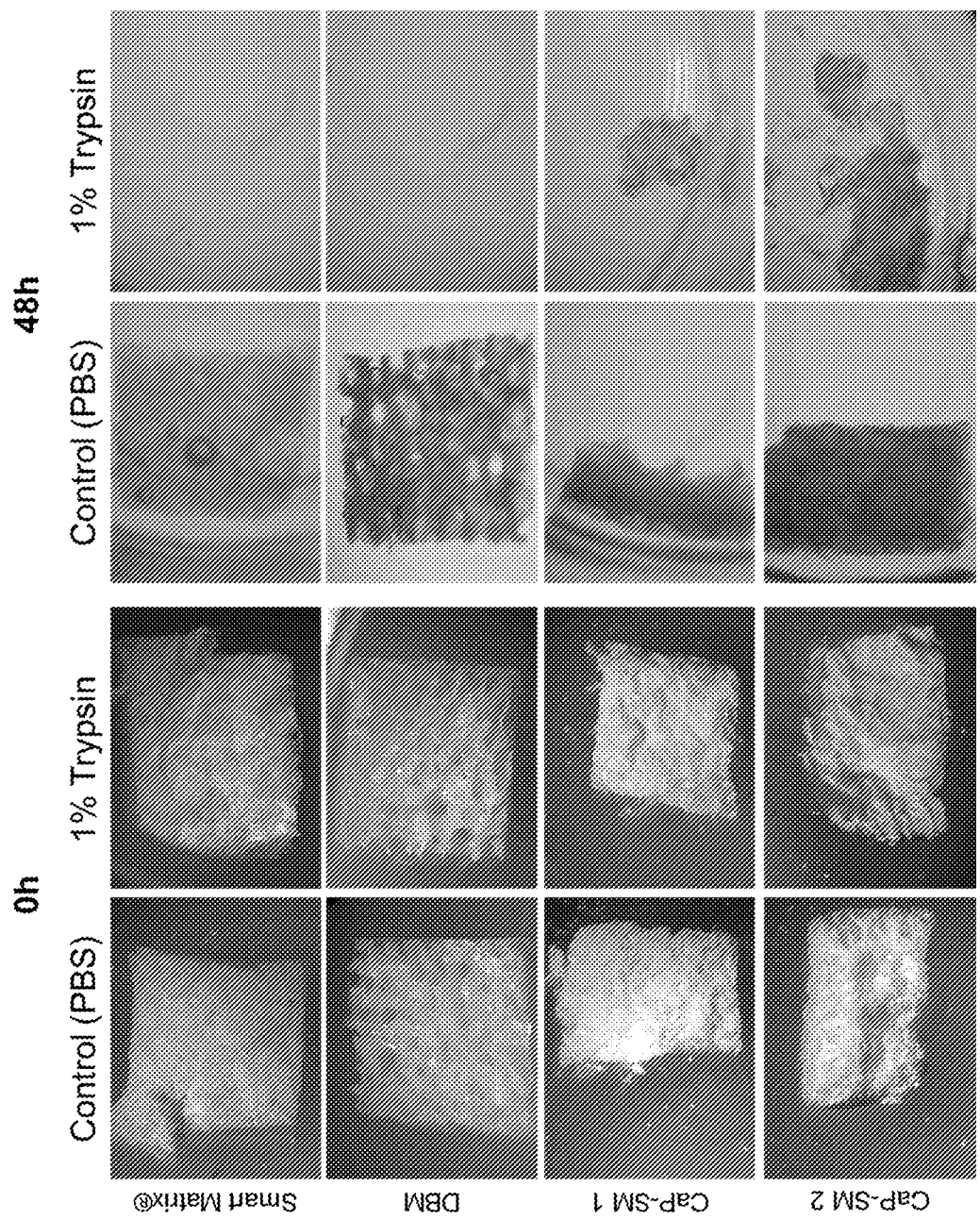
Figure 15:
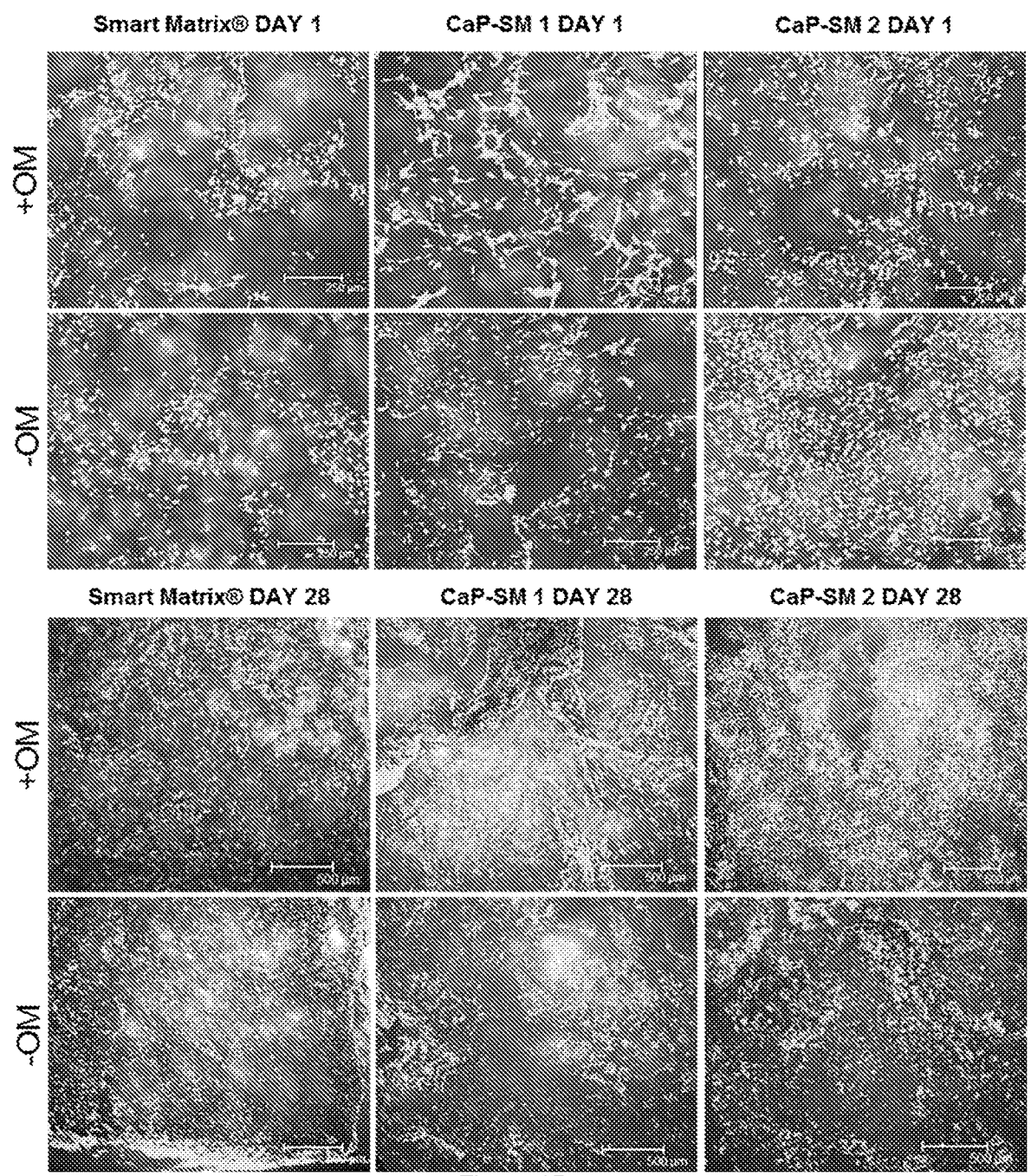
Figure 16:
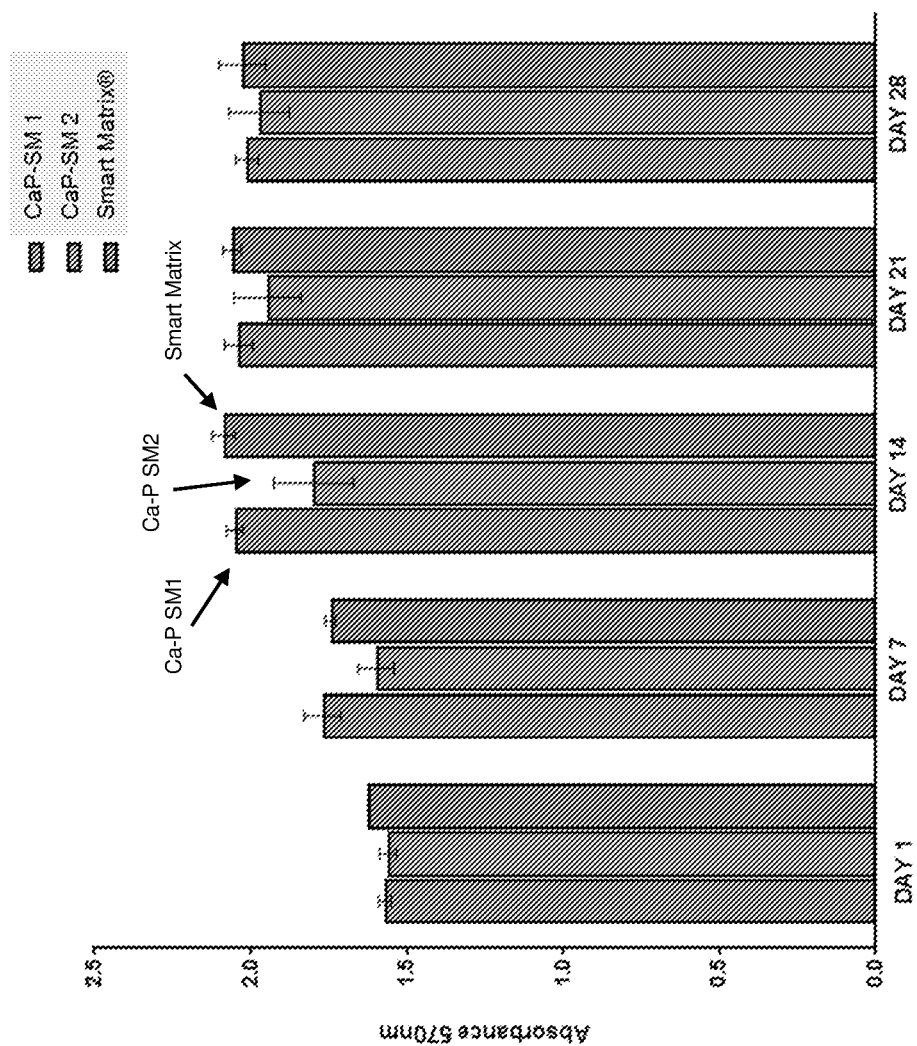
Figure 17:
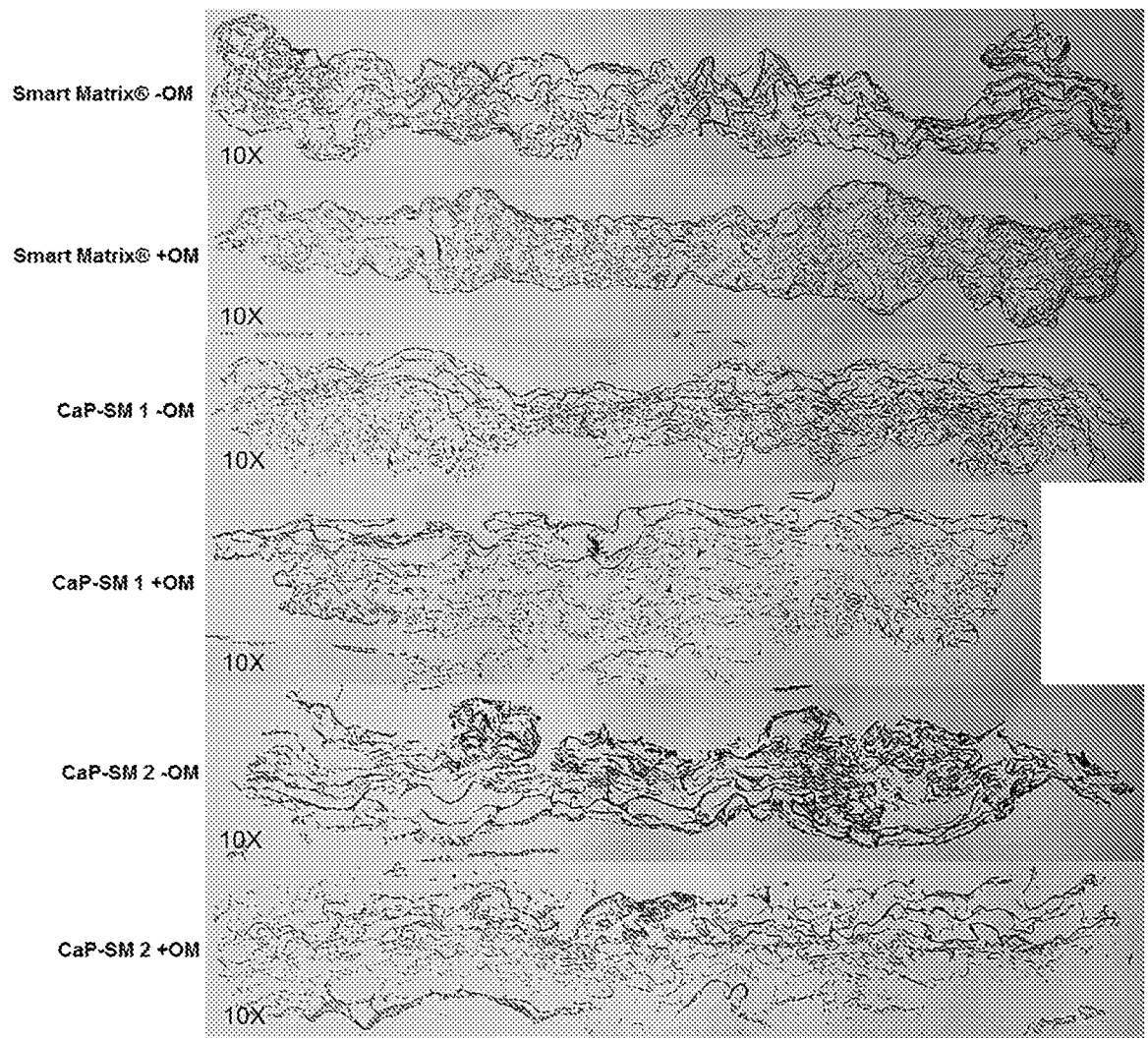
Figure 18:
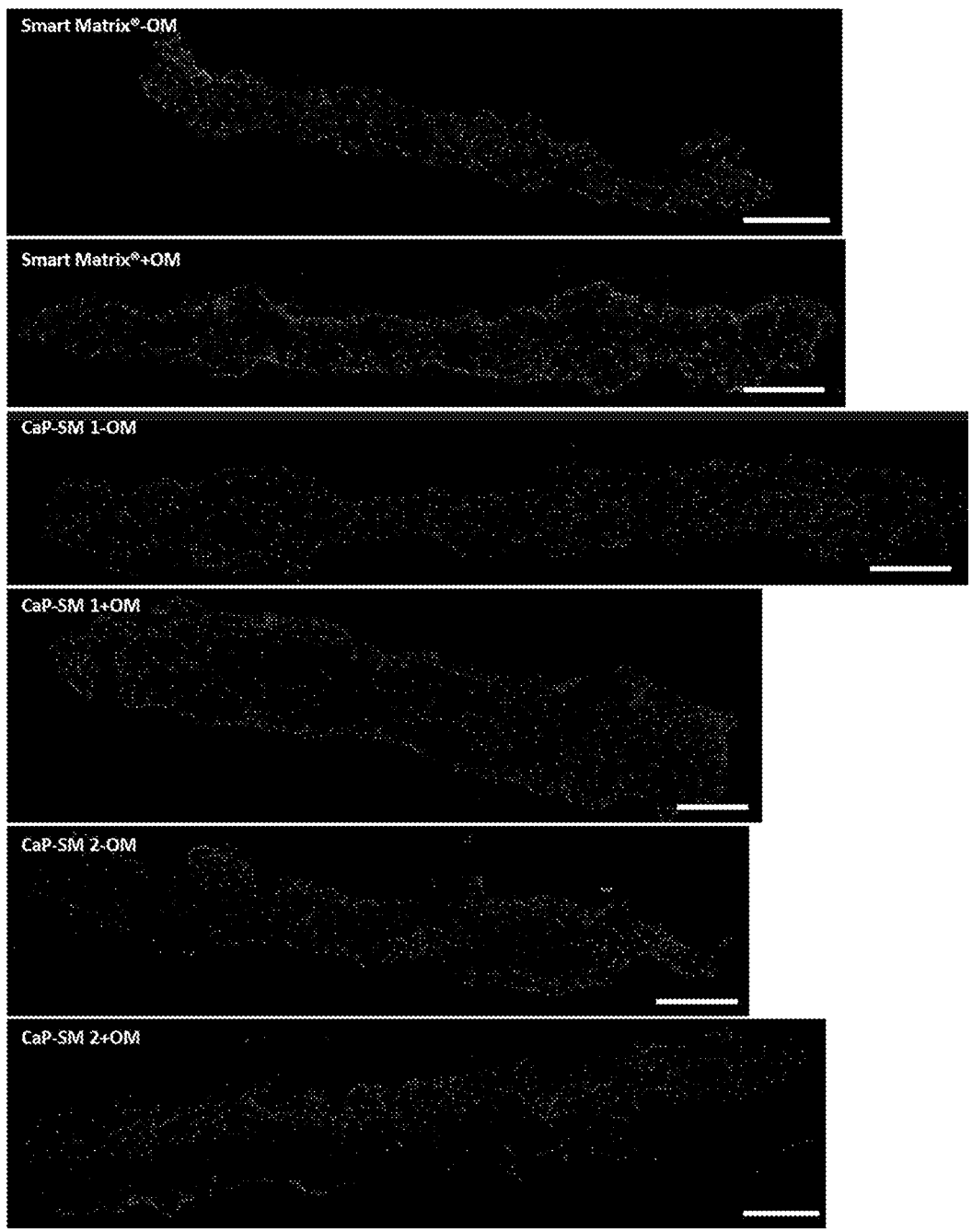
Figure 19:
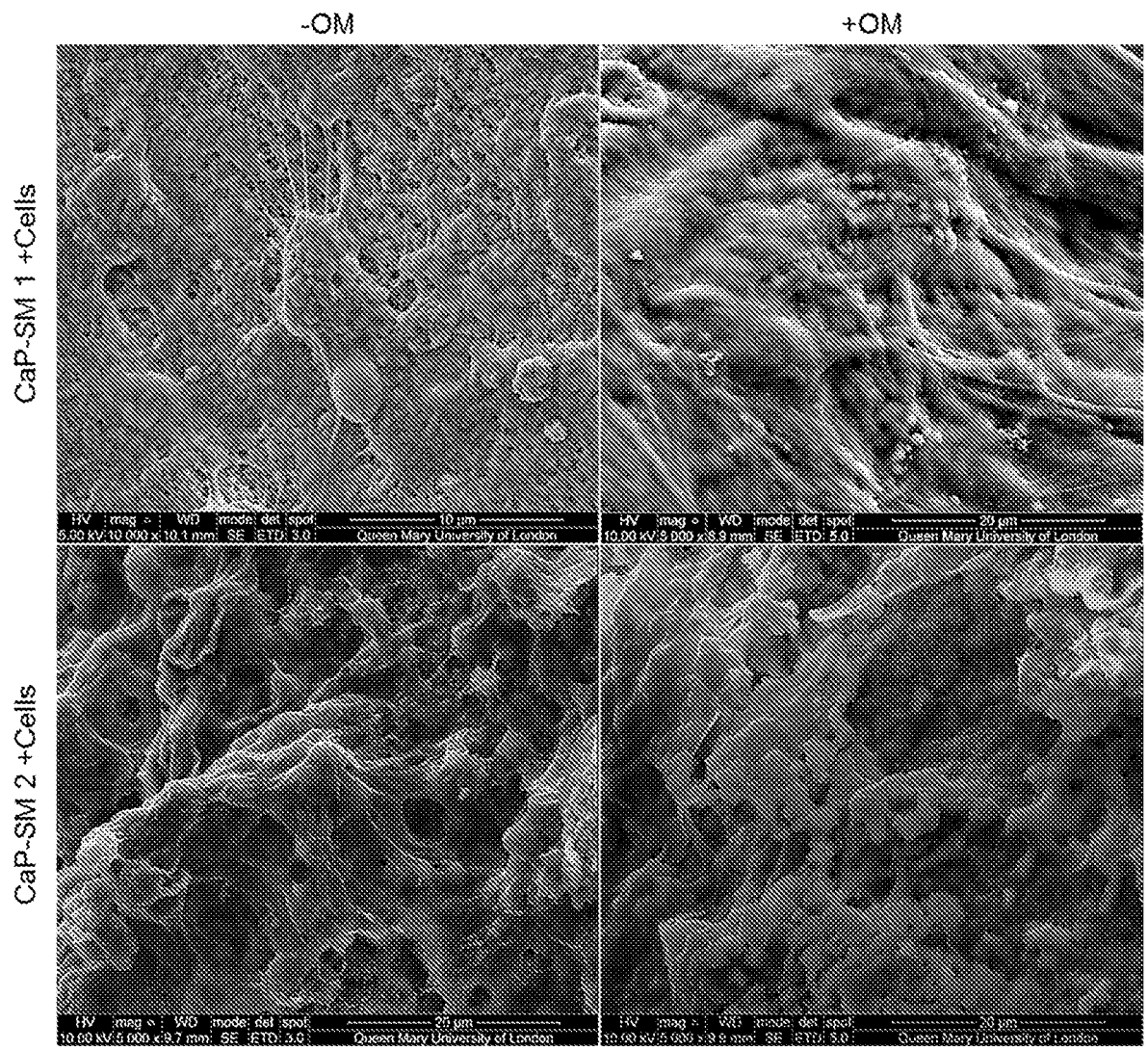
Figure 20:
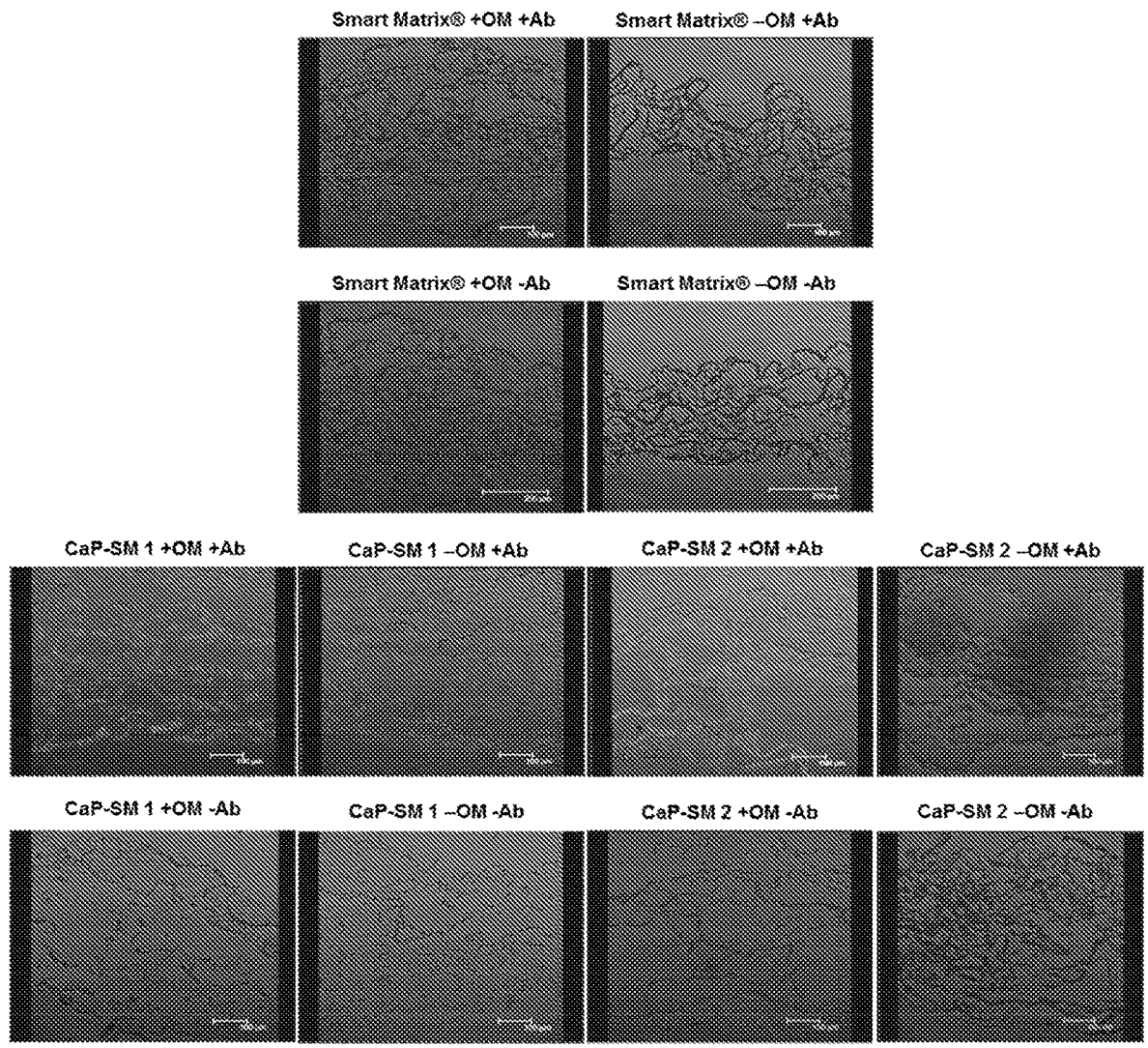
Figure 21:
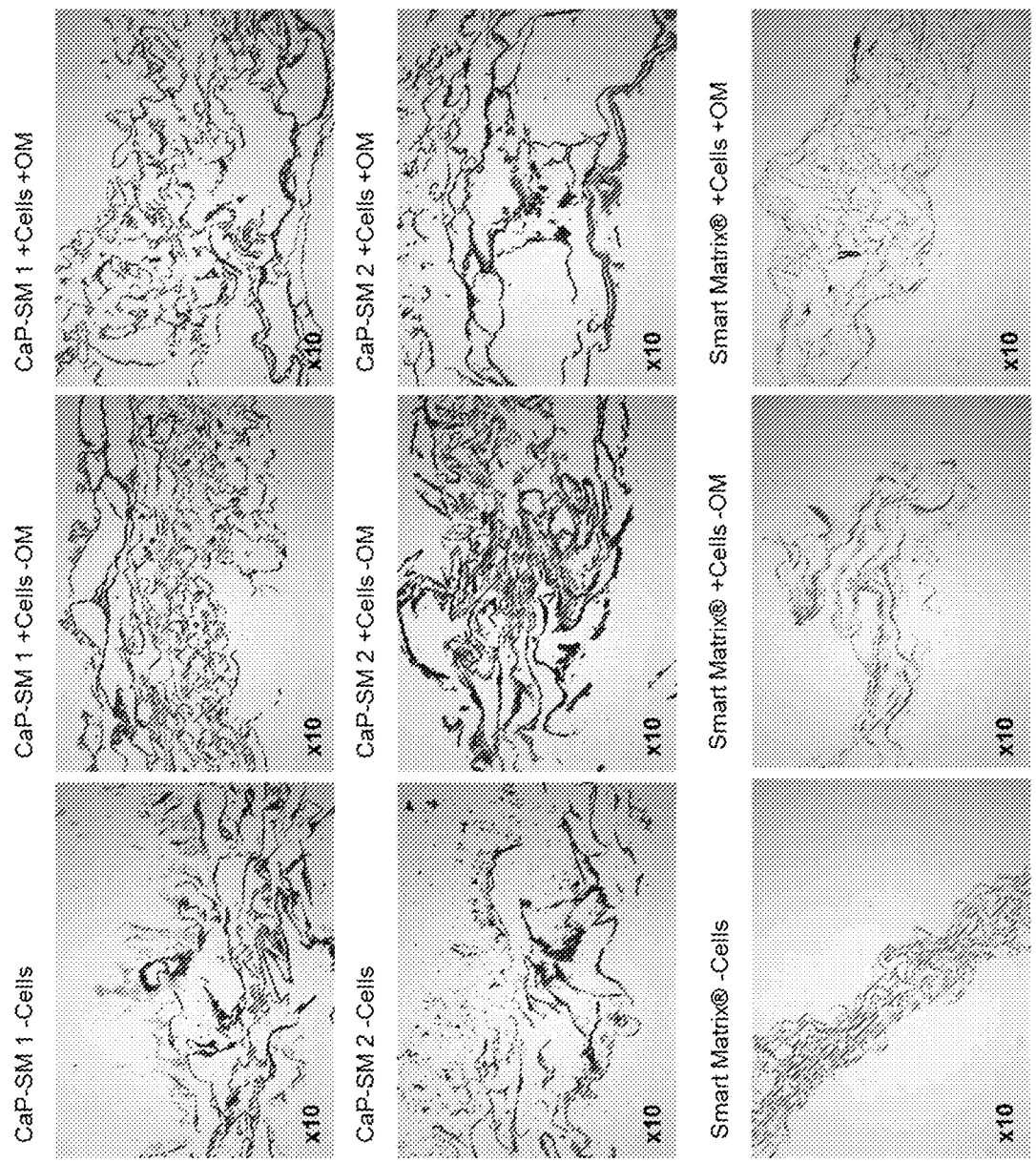
Figure 22:
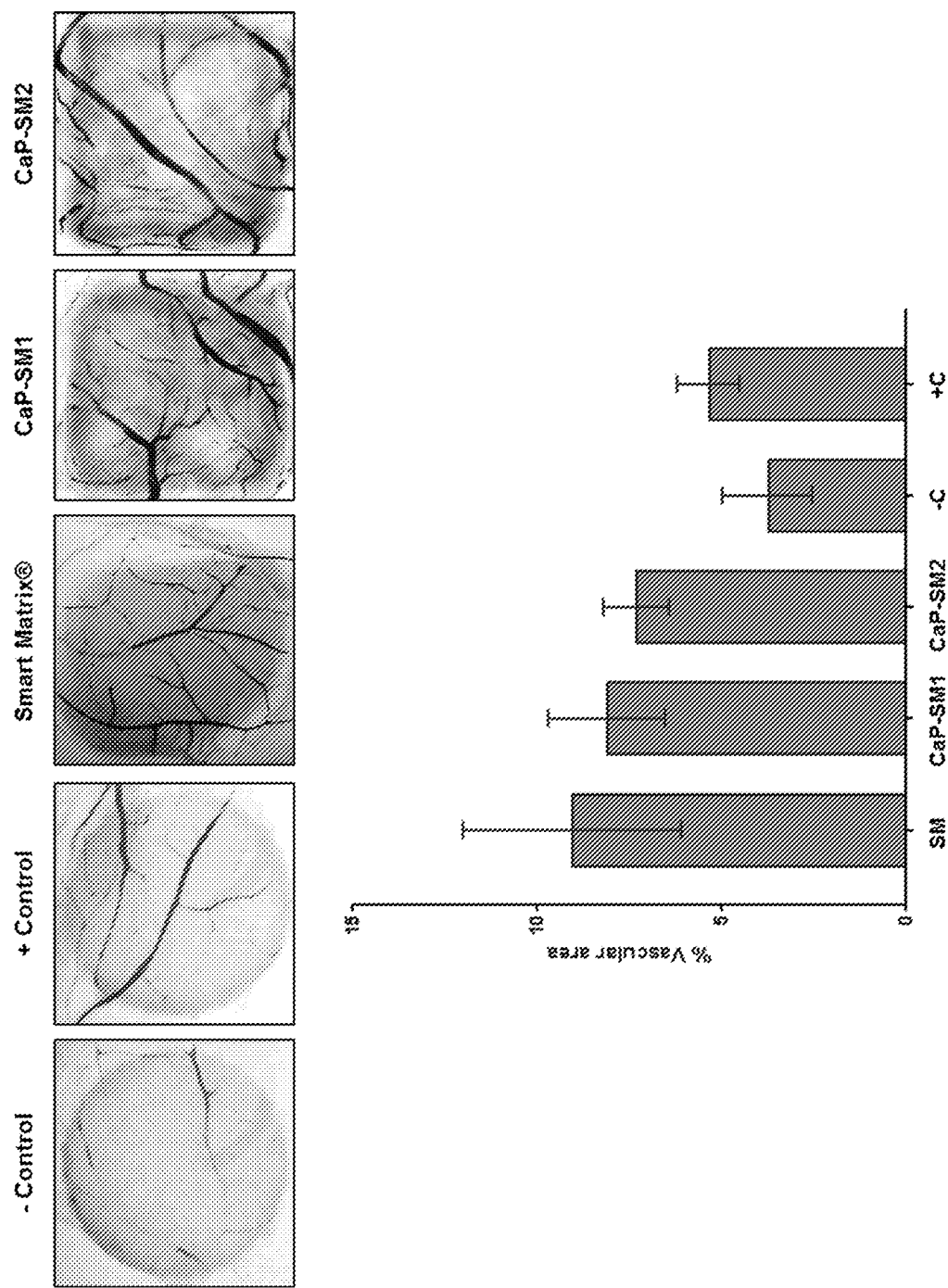

FIG. 8 shows alamarBlue® assay results (*p<0.05). Results show average±standard deviation;

FIG. 9 shows H&E staining of cross-sections of seeded CaP-SM scaffolds with human dermal fibroblasts after 10 days of culture. Top left, Smart Matrix® (20× magnification); top right, CaP-SM after 2 days of immersion in SBF (40× magnification); bottom left, CaP-SM after 6 days of immersion in SBF (40× magnification); and bottom right, CaP-SM after 9 days of immersion in SBF (40×magnification). Although it may not be visible in black and white versions of this figure, the scaffold is stained bright pink while the cells appear stained purple;

FIG. 10 shows SEM photographs of CaP-SM1, CaP-SM2, SM1 and SM2;

FIG. 11 shows EDX elemental analysis of the main elements in the mineral deposits of CaP-SM1, CaP-SM2, SM1 and SM2;

FIG. 12 shows FTIR representative spectra for CaP-SM, SM1 and SM2 scaffolds;

FIG. 13 shows Von Kossa staining of scaffolds for SM1, SM2, CaP-SM1 and CaP-SM2;

FIG. 14 shows photographs of In vitro bio-degradation using 1% trypsin of CaP-SM1 and CaP-SM2 scaffolds;

FIG. 15 shows results from the Live/Dead assay at days 1 and 28 undertaken with MC3T3-E1 osteoprogenitor cells. +OM indicates osteogenic medium while −OM indicates standard medium (without osteogenic supplements);

FIG. 16 shows alamarBlue® assay results over 28 days of culture period in osteogenic medium for Smart Matrix®, CaP-SM 1 and CaP-SM 2 seeded scaffolds, undertaken with MC3T3-E1 osteoprogenitor cells. Results display average±standard deviation;

FIG. 17 shows H&E staining of seeded scaffolds after 28 days in culture either under standard (−OM) or osteogenic (+OM) conditions, undertaken with MC3T3-E1 osteoprogenitor cells. Although it may not be visible in black and white versions of this Figure, nuclei of the cells are seen in dark purple with surrounding pink cytoplasm while the scaffolds are stained pink/dark pink;

FIG. 18 shows DAPI stained sections of MC3T3-E1 seeded Smart Matrix®, CaP-SM1 and CaP-SM2 scaffolds after 28 days in culture under either standard (−OM) or osteogenic (+OM) conditions. Although it may not be visible in black and white versions of this Figure, nuclei of cells can be seen in fluorescence blue colour. Scale bar is 500 µm;

FIG. 19 shows representative SEM images of seeded scaffolds after 28 days in culture either under standard (−OM) or osteogenic (+OM) conditions, undertaken with MC3T3-E1 osteoprogenitor cells;

FIG. 20 shows immunostaining of osteopontin in MC3T3 seeded scaffolds after 28 days in culture either under standard (−OM) or osteogenic (+OM) conditions. Although it may not be readily visible from black and white versions of this figure, red fluorescence indicates presence of osteopontin, blue fluorescence indicates cell nuclei;

FIG. 21 shows Von Kossa staining of MC3T3 seeded scaffolds after 28 days in culture either under standard (−OM) or osteogenic (+OM) conditions. Although it may not be readily visible from black and white versions of this figure, black/dark brown indicates CaP deposits while pink indicates fibrin fibres; and FIG. 22 shows (top) representative macroscopic images of the different scaffolds and controls; and (bottom) percentage of vascular area (mean±standard error of the mean) for scaffolds and controls. No statistical significances were found between the 3 scaffolds.

EXAMPLE 1

Materials and Methods

Preparation of Smart Matrix®

The manufacturing process of Smart Matrix takes place in 3 distinct stages:

1) vigorous mixing (4000 rpm) of pre-warmed (37° C.) reagents to form a white foam that is cast into a mould and incubated at 37° C. for 1 h to allow clotting 2) chemical crosslinking with 0.2% vol/vol glutaraldehyde (Sigma-Aldrich, UK) in 80% absolute ethanol/20% MES buffer for 4 h at room temperature, followed by 1× wash with $diH_2O$ (10 min), 1× wash with 0.1% wt/vol $NaBH_4$ (Sigma-Aldrich, UK) in $diH_2O$ (overnight), 5× washes with 0.1% wt/vol $NaBH_4$ in $diH_2O$ (10 min), and 5× washes with $diH_2O$ (10 min) to eliminate any possible residue of glutaraldehyde and its reducing agent $NaBH_4$ 3) lyophilisation of the scaffolds at −40° C. for 36 h (Virtis Genesis Freeze Dryer, Biopharma, UK), Reagents mixed in the first stage are:
3 ml of 2% wt/vol alginate (Novamatrix, Norway) in MES buffer pH=7.4
25 µl of 1M $CaCl_2$ (Sigma-Aldrich, UK) in $diH_2O$
6 ml of 2% wt/vol dialysed human fibrinogen (Ria-STAP®, CSL Behring Ltd., UK) (Sharma et al. 2015) or bovine fibrinogen (Sigma-Aldrich, UK) in MES/NaCl buffer pH=7.4
750 µl of surfactant mix [20% wt/vol Pluronic F-68 (Sigma-Aldrich, UK) in $diH_2O$, 20% wt/vol decyl-β-d-maltopyranoside (Sigma-Aldrich, UK) in $diH_2O$, 20% wt/vol dodecyl-β-d-glucopyranoside (Sigma-Aldrich, UK) in $diH_2O$, and 20% wt/vol octyl-β-d-maltopyranoside (Sigma-Aldrich, UK) in $diH_2O$] (WO2013164635 A1).
1.2 ml of 10I.U./ml human thrombin (TISSEEL®, Baxter International Inc., US) or dialysed bovine thrombin (Sigma-Aldrich, UK) in HEPES/NaCl buffer pH 7.4
1.5 ml of 66% wt/vol trehalose (Fisher Scientific, UK) in $diH_2O$ Preparation of Calcium Phosphate-Smart Matrix® (CaP-SM) by Immersion in Simulated Body Fluid (SBF):

SBF solution was prepared according to the protocol described by Kokubo et al. 1990. SBF solution contained a defined concentration of relevant ions (Table 1):

TABLE 1

Concentration of relevant ions in SBF solution.

| Ion | $Na^+$ | $K^+$ | $Mg^{2+}$ | $Ca^{2+}$ | $Cl^-$ | $HCO_3^-$ | $HPO_4^{2-}$ |
|---|---|---|---|---|---|---|---|
| mM | 142 | 5 | 1.5 | 2.5 | 148.8 | 4.2 | 1 |

To prepare the SBF solution, the following quantities and reagents were added to 0.4 L of $dH_2O$: 0.152 g of $MgCl_2$-6H2O; 0.176 g of $NaHCO_3$; 0.114 g of $K_2HPO_4.3H2O$; 0.139 g of $CaCl_2$; 0.112 g of KCl and 4.027 g of NaCl. The solution was vigorously stirred for 10 min. The pH was adjusted to 7.25 with $(CH_2OH)_3CNH_2$ 50 mM/HCl 45 mM buffer. Finally, the volume was topped up to 0.5 L with $dH_2O$ and the solution was vigorously stirred for 10 min.

1 cm×1 cm Smart Matrix® scaffolds were immersed in SBF for up to 9 days at 37° C. SBF solution was changed every 2-3 days. After the immersion time, scaffolds were removed from the SBF solution, washed with $dH_2O$, frozen at −80° C. and lyophilised.

Scanning Electron Microscopy (SEM) and Energy Dispersive X-Ray Spectroscopy (EDX)

SEM and EDX analysis were conducted at the Nanovision Centre at Queen Mary's University of London.

Lyophilised CaP-SM samples after 0, 2, 4, 6 and 9 days of immersion in SBF were gold sputtered coated before observation under SEM and EDX analysis.

SEM microphotographs were taken at 150×, 500×, 2,000×, 10,000×, 20,000× and 40,000× magnifications and obtained at 5 kV. Morphology of scaffolds, qualitative pore size, morphology and size of CaP crystal deposits were studied from the SEM images. Elemental analysis of the CaP-SM scaffolds and Ca/P ratio were studied from the EDX spectra that were obtained at 10 kV.

Von Kossa Staining of Cross-Sections:

CaP-SM scaffolds were embedded in paraffin and cross-sections cut to a thickness of 4 µm using a microtome.

The principle of the Von Kossa staining is a precipitation reaction in which silver ions react with phosphate under acidic conditions. Then, photochemical degradation of silver phosphate to silver occurs under light illumination. A 1.5% silver nitrate solution was prepared by adding 1.5 g of $AgNO_3$ to 100 ml of $dH_2O$. Similarly, a 2.5% sodium thiosulphate solution was prepared by adding 2.5 g of $Na_2S_2O_3$ to 100 ml of $dH_2O$.

Slides were covered with 1.5% silver nitrate solution and expose to bright light for 1 h (under a lamp), after which they were washed with $dH_2O$. Then slides were covered with 2.5% sodium thiosulphate for 5 min and dipped in running water before immersion in Eosin counter stain for 5 min. Slides were dipped in 70% IMS, then 90% IMS and immersed in 100% IMS for 1 min. Finally, they were immersed in Xylene for 2 min, dipped twice in Xylene, left to dry and coversliped for observation under light microscopy. CaP deposits were stained black/dark brown while Smart Matrix® was stained pink/red.

In Vitro Bio-Degradability (Trypsin Digestion)

1 cm×1 cm CaP-SM scaffolds (n=3 per time of immersion in SBF) were placed in a 12 well plate. To each well containing a scaffold disc 2.5 ml of a 0.25% trypsin in versene solution was added and the plate incubated at 37° C. with 5% $CO_2$. At 0, 2, 4, 6, 24, 48, and 168 h (7 days) a 100 µl aliquot from each well was transferred to an eppendorf tube and stored at −80° C. Each well was replenished with 100 µl of fresh 0.25% trypsin in versene solution.

A total protein colorimetric assay was performed on the 100 µl aliquots. A standard curve of bovine serum albumin in PBS from 0.1 to 1.5 mg/ml was prepared. Aliquots were allowed to thaw before 50 µL from the aliquots and standards were mixed with 750 µl of BradfordUltra™ solution in a cuvette. Following the manufacturer's instructions, absorbance at 595 nm was measured against air in a M550 double beam UV/visible spectrophotometer (Spectronic Camspec Ltd., UK). Absorbance at 595 nm for the 0 time point was subtracted from the other samples. A standard curve was plotted and used to calculate the percentage of matrix protein in solution considering that, if completely degraded, a 1×1 cm piece of the scaffolds would have 4 mg/ml of protein in solution.

Cell Viability by AlamarBlue® Assay:

Primary normal human dermal fibroblasts from three different donors were used. Cells were isolated and cultured as previously described (Sharma et al. 2015).

CaP-SM in SBF for 0, 2, 6 and 9 days were used for this study as SEM shows that after 2 days of immersion in SBF CaP deposits are up to 0.2 µm in size while at days 6 and 9 they are 0.05-0.8 µm-larger aggregates. Besides, more CaP is observed after 9 days in SBF than after 6 days. Therefore, the effect of CaP deposits size and CaP concentration on cell viability were observed in this study.

1 cm×1 cm CaP-SM scaffolds were transferred to 24 well plates along with plastic coverslips (monolayer control) and washed once with IMS followed by 4× with PBS. 3 scaffolds per cell population were used, therefore n=9.

$0.5 \times 10^6$ cells were seeded per scaffold at passage 5 and after 3 h incubation at 37° C. with 5% $CO_2$ to allow the cells to attach to the scaffolds, 2 mL of medium were added per well.

At days 1, 2, 4, 7 and 10 of culture an alamarBlue® assay was performed: 1 ml of alamarBlue® working solution (diluted 10× from stock solution with phenol free DMEM) were added per well and samples incubated at 37° C. with 5% $CO_2$ for 4 h, after which each well content was transferred to a cuvette and absorbance measured at 570 nm in a uv/vis spectrophotometer.

Results were statistically analysed by one-way ANOVA using Sigma Stat 3.5 software. A $p<0.05$ was considered a significant result.

Cell Migration through the CaP-SM

Seeded CaP-SM scaffolds after 10 days of culture were fixed in 4% paraformaldehyde and processed for paraffin histology. Cross-sections were cut to a thickness of 4 µm using a microtome.

Sections were stained with a classic Haematoxylin & Eosin staining, which stains cells purple/black while the background appears bright pink.

Stained sections were dried and coverslipped for observation under light microscopy.

EXAMPLE 2

Results

SEM and EDX Analysis

Figure 1:
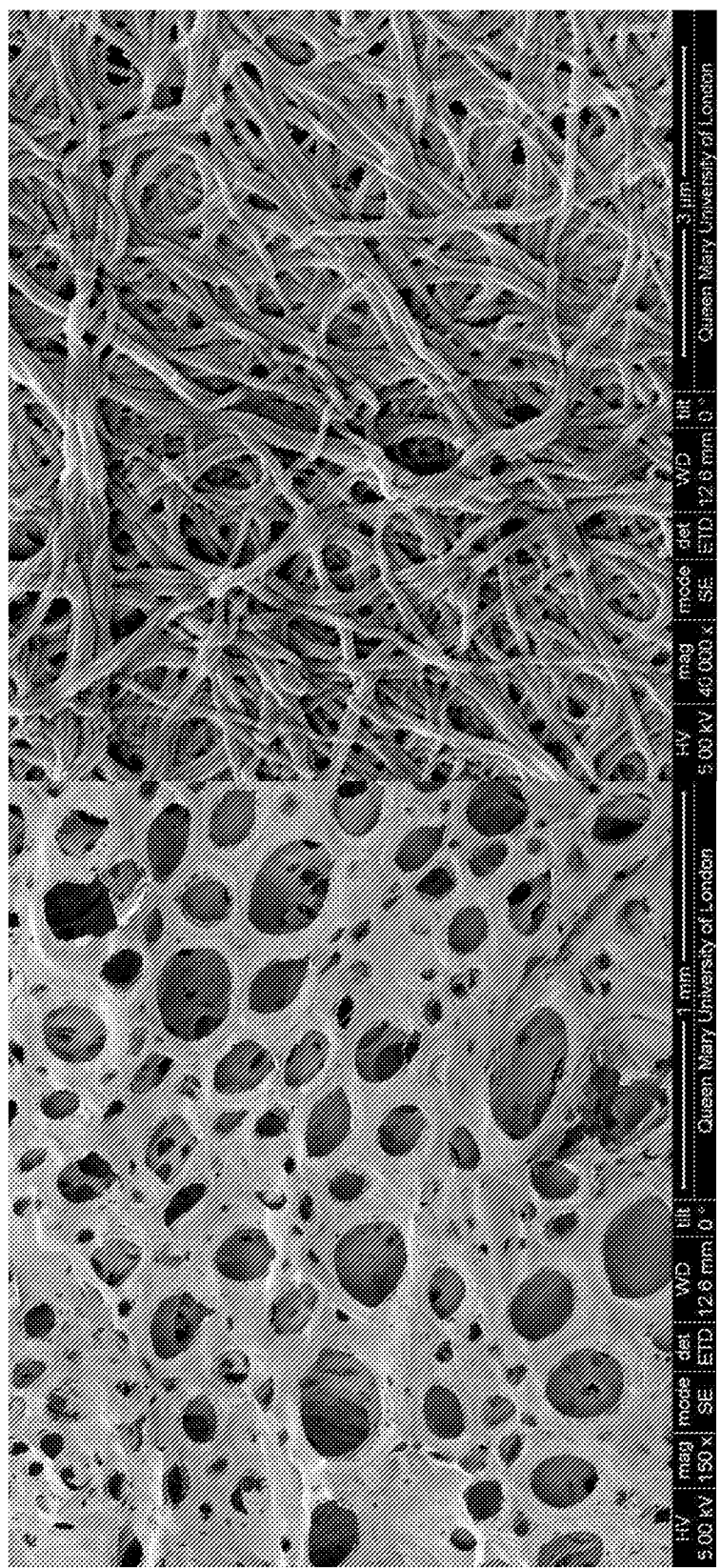

SEM images in FIG. 1 show that Smart Matrix® is a uniform and homogeneous material composed of fibres. It possesses micro (30-350 µm) as well es nano-porosity (0.06-0.6 µm). Pores appear to be interconnected.

Figure 2:
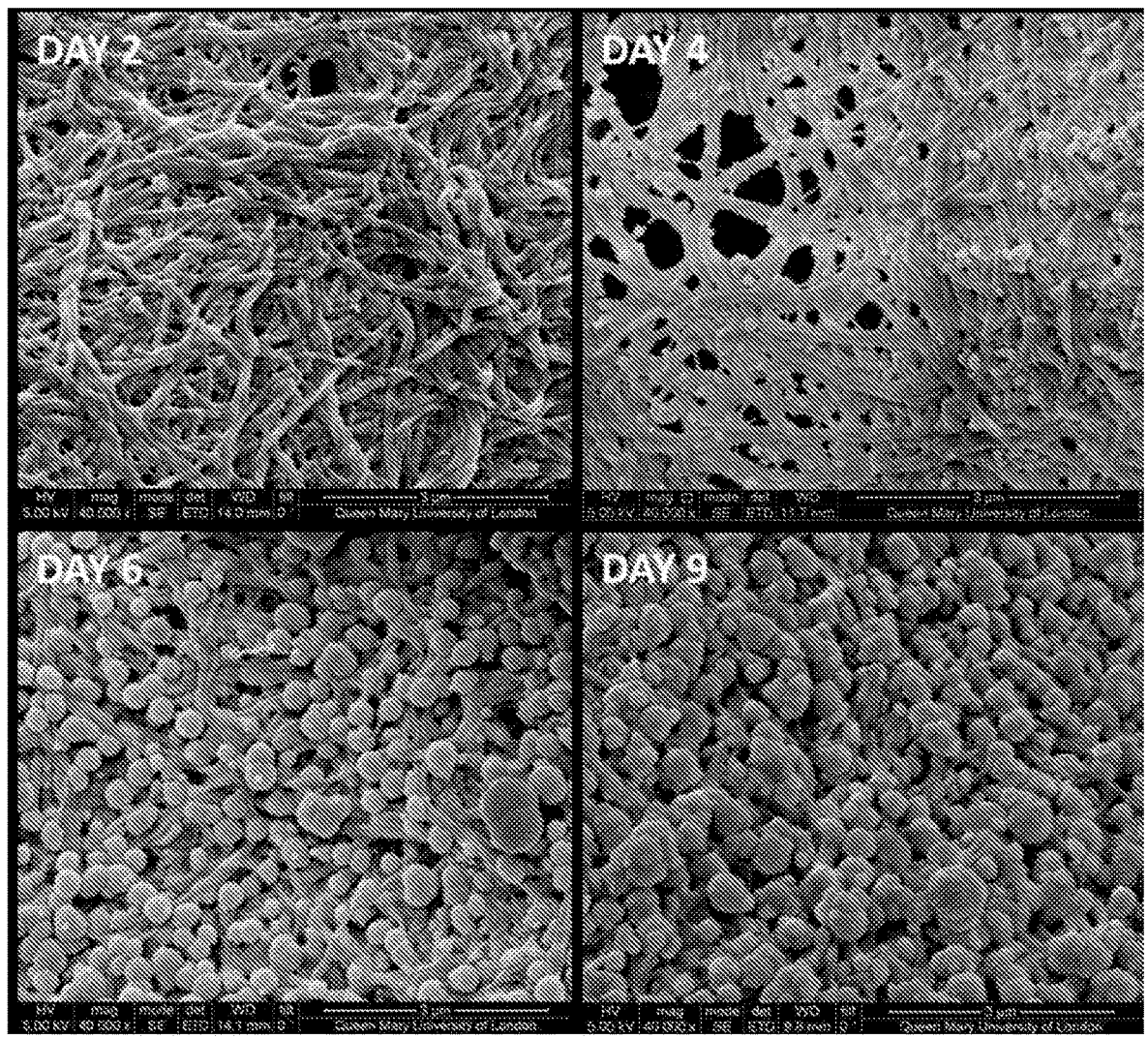

SEM images displayed FIG. 2 show mineral deposition over time: after 2 days of immersion in SBF globular mineral deposits of up to 0.2 µm in size are observed: after 4 days of immersion in SBF globular mineral crystals are observed on the surface of the fibrin/alginate matrix, which grow with increasing immersion time; after 6 days of immersion in SBF globular mineral crystals (0.05-0.8 µm-larger aggregates) are observed on the entire surface for the biomaterial.

Although an increase in crystal size is seen with increasing immersion time in SBF solution, fibrin fibres are still visible after 9 days of immersion in SBF, as it can be seen from FIG. 2 bottom right. This suggests that the beneficial pro-angiogenic and bioactive properties of fibrin would not be masked by the presence of the crystals.

Figure 3:
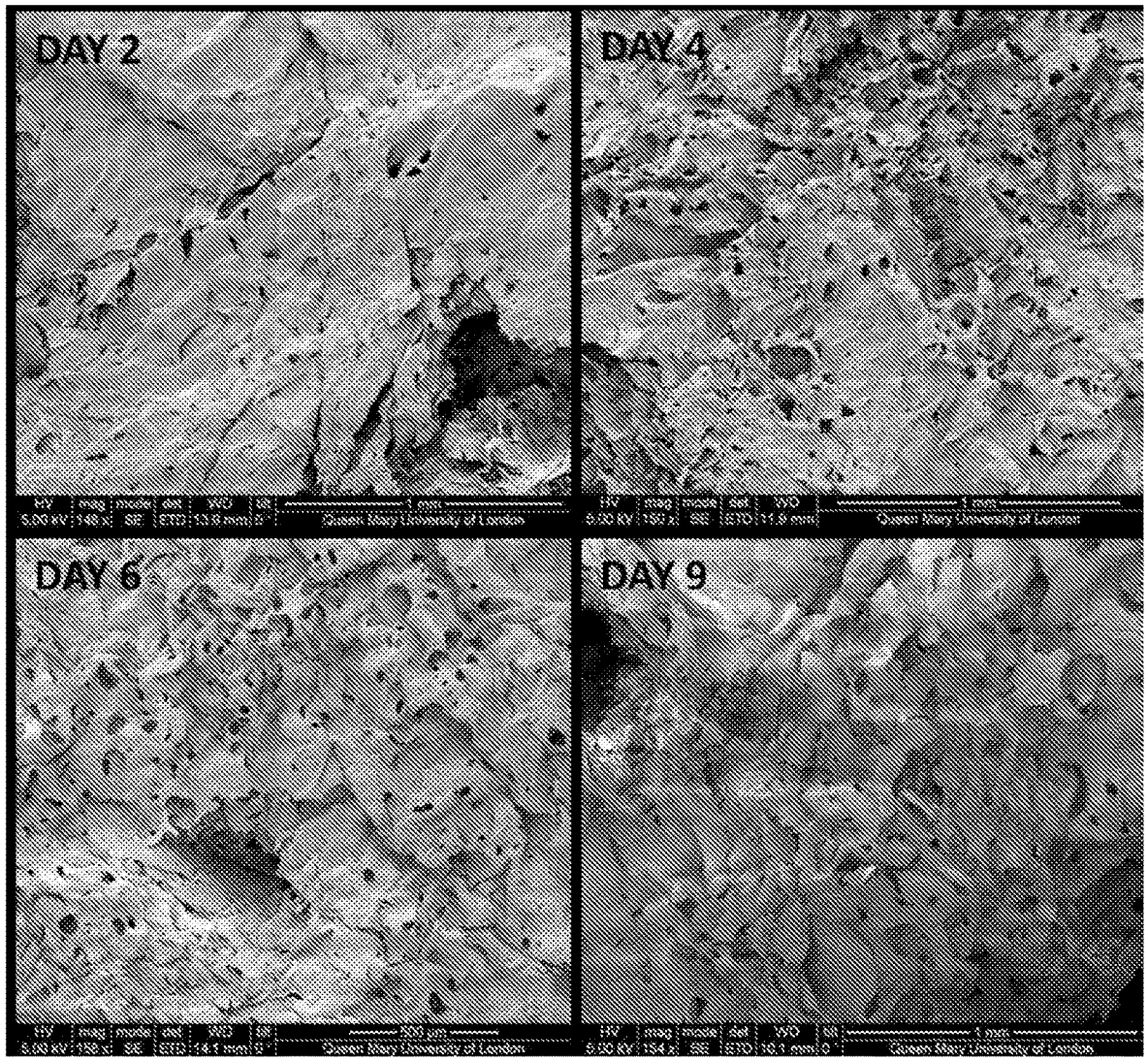
Figure 4:
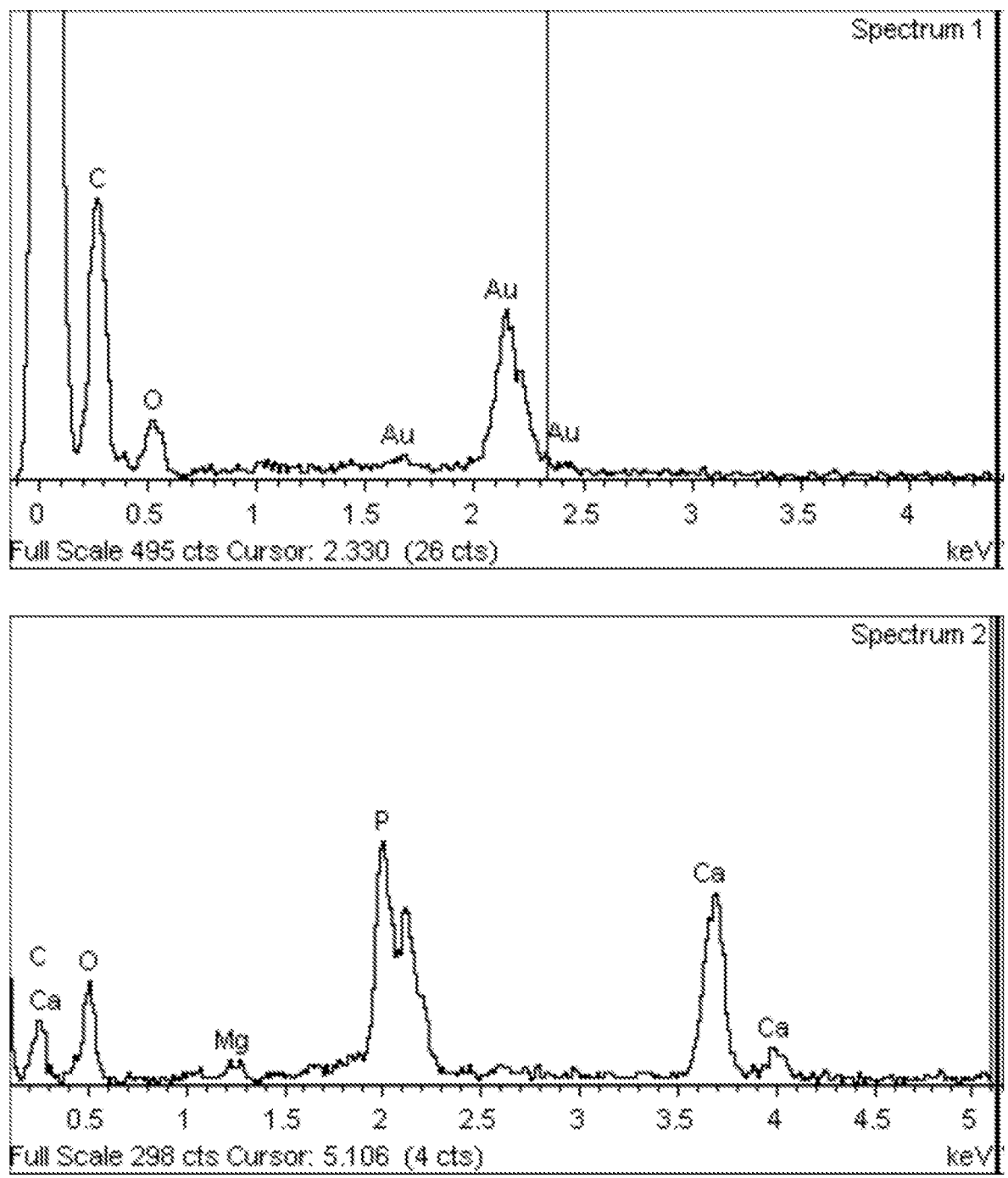
FIG. 4 shows EDX analysis of Smart Matrix® (Spectrum 1) and CaP-SM after 6 days of immersion in SBF (Spectrum 2) showing that Ca and P are the main elements of the CaP deposits that also contain Mg.

FIG. 3 images show low magnification photos of CaP deposition over time, suggesting that the original microporosity found in Smart Matrix® is reduced upon immersion in SBF, as the reduction is noticeable after only 2 days of immersion in SBF (FIG. 3, top left):

EDX analysis (FIG. 4) of CaP-SM after 6 days of immersion in SBF shows that Ca and P are the main elements of the globular crystals, also at day 9. Before day 6 no Ca and P are detected in the EDAX spectra. Calculated Ca/P was 1.7±0.6 (average±standard deviation; Ca/P for hydroxyapatite is 1.67). Mg is also present: SBF contains $Mg^{2+}$ and $Mg^{2+}$ is among the reported substituting ions present in bone mineral (Wopenka and Pasteris 2005; LeGeros 2008).

Von Kossa Staining of Cross-Sections

Figure 5:
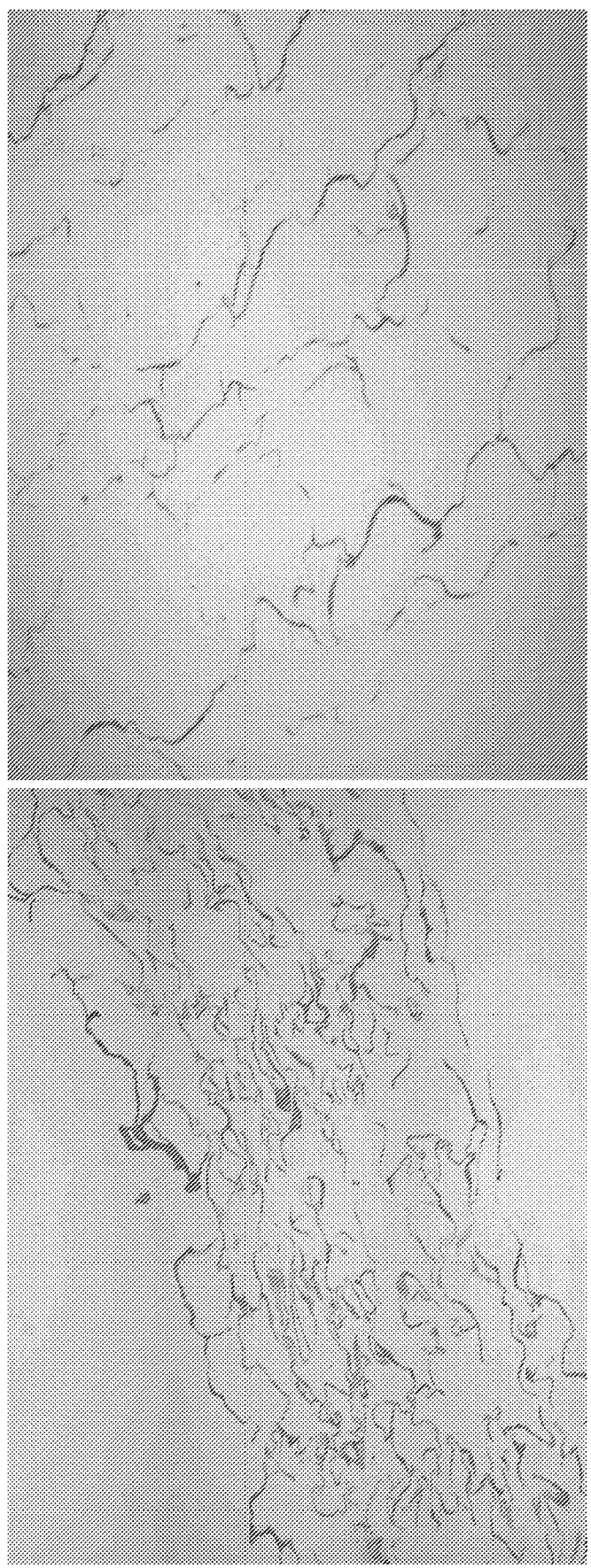
FIG. 5 shows eosin staining of the Smart Matrix® scaffold used in this study (4× magnification) (left). Von Kossa staining with eosin counterstaining (10× magnification) (right)

FIG. 5 shows eosin staining of Smart Matrix® scaffold used (left) and a Von Kossa stained scaffold, counterstained with eosin (right). As can be seen, Smart Matrix® appears darker after the Von Kossa staining. The homogeneous open pore structure of the scaffold can also be seen as already observed in the SEM photos:

FIG. 6 shows the Von Kossa staining results of CaP-SM scaffolds after immersion in simulated body fluid (SBF) for up to 9 days. Samples were counterstained with eosin. CaP deposits are stained black/dark brown while Smart Matrix® stains pink/red.

As observed from the photographs, the scaffold fibres appear darkened with immersion in SBF. Black/brown staining seems to increase with longer immersion periods in SBF. It is also interesting to note that the CaP deposits are found throughout the scaffold structure, which appears homogeneously stained. These results suggest that even deposition of CaP deposits throughout Smart Matrix® can be achieved with a biomimetic procedure of immersion of scaffolds in SBF.

In Vitro Bio-Degradability (Trypsin Digestion)

FIG. 7 shows that the in vitro degradation rate of the scaffolds decreases as the immersion time in SBF increases. The degradation rate is especially decreased in the first 6 h when compared to Smart Matrix®. These results suggest that CaP-SM would take longer to degrade in vivo than Smart Matrix®, which has been observed in histological sections up to 5-6 weeks after implantation in a full thickness skin wound in a porcine model. It has been suggested that new bone formation in vivo takes up to 4 months (Hadjidakis and Androulakis 2006), so a slower degradation of CaP-SM is expected to be beneficial for bone repair.

Cell Viability by AlamarBlue® Assay

Results displayed in FIG. 8 show that cells are able to grow and proliferate on the CaP-SM scaffolds, suggesting that the CaP deposited by the biomimetic method is not toxic to the cells.

There is a significant difference ($p<0.05$) between the monolayer control and cells on scaffolds until day 4, at day 7 only for CaP-SM 2 and 6 and then no significant difference at day 10. This may be due to an inefficient cell seeding on the 3D scaffolds compared to the flat control where the seeding efficiency is of 100%. As the culture period progresses cells in the 3D scaffolds proliferate more than on the flat control. Finally, there is no statistical differences between Smart Matrix® and the CaP-SM scaffolds, suggesting that the beneficial cellular properties of Smart Matrix® are still present in CaP-SM scaffolds.

Cell Migration through the CaP-SM

Photographs in FIG. 9 show that primary normal human dermal fibroblasts were able to migrate through the CaP-SM scaffolds and after 10 days of culture populated the scaffolds throughout.

EXAMPLE 3

Materials and Methods for Forming Alternative Scaffolds

Alternative scaffolds were formulated by immersing Smart Matrix@ in SBF solutions as described below.

Table 2 describes the concentration of relevant ions present in the SBF solutions:

TABLE 2

Concentration of relevant ions in SBF solution.

| Solution | Ion | $Na^+$ | $K^+$ | $Mg^{2+}$ | $Ca^{2+}$ | $Cl^-$ | $HCO_3^-$ | $SO_4^{2-}$ | $HPO_4^{2-}$ |
|---|---|---|---|---|---|---|---|---|---|
| SBF-1 | mM | 766.3 | 35.9 | 10.9 | 18.8 | 740.9 | 71.5 | 3.6 | 7.1 |
| SBF-2 | mM | 686.1 | 31.2 | 9.3 | 15.6 | 728.6 | 26.1 | — | 6.2 |
| SBF-3 | mM | 660 | 12.4 | — | 15.6 | 691.3 | — | — | 6.2 |

To prepare the SBF-1 solution, the following quantities and reagents were added to 0.7 L of $dH_2O$: 1.465 g of $CaCl_2$; 1.555 g of $MgCl_2.6H_2O$; 2.520 g of $NaHCO_3$ and 1.150 g of $K_2HPO_4.3H_2O$. Following this, the pH of the solution was adjusted to 6.0 using 1M HCl, after which, 0.360 g of $Na_2SO_4$, 1.125 g of KCl 27.015 g of NaCl and 2.130 g of $Na_2CO_3$ were added to the solution. Finally, the pH of the solution was adjusted to 6.5 using 1M HCl.

To prepare the SBF-2 solution, the following quantities and reagents were added to 0.4 L of $dH_2O$: 0.695 g of $CaCl_2$; 0.760 g of $MgCl_2.6H_2O$; 0.880 g of $NaHCO_3$ and 0.570 g of $K_2HPO_4.3H_2O$. Following this, the pH of the solution was adjusted to 6.0 using 1M HCl, after which, 0.560 g of KCl and 20.135 g of NaCl were added to the solution. Finally, the pH of the solution was adjusted to 6.5 using 1M NaOH.

To prepare the SBF-3 solution, the following quantities and reagents were added to 0.4 L of $dH_2O$: 20.135 g of NaCl; 0.695 g of $CaCl_2$ and 0.570 g of $K_2HPO_4.3H_2O$. The pH of this solution was adjusted to 6.0 with 1M HCl.

All solutions were filtered with 0.22 μm PES membrane before use.

1 cm×1 cm Smart Matrix® scaffolds were immersed in either SBF-1 or SBF-2 solution for 24 hours with constant stirring at 160 rpm on an orbital shaker at 37° C. After the immersion time, scaffolds were removed from the SBF solutions, washed with $dH_2O$ in an ultrasonic water cleaner for 60 seconds, frozen at −80° C. and lyophilised.

Lyophilised scaffolds can be further immersed in SBF-3 for 48 hours with constant stirring at 80 rpm on an orbital shaker at 37° C. After the immersion time, scaffolds are removed from the SBF-3 solution, washed with $dH_2O$ in an ultrasonic water cleaner for 60 seconds, frozen at −80° C. and lyophilised.

Key:
- SM1: Smart Matrix® scaffolds immersed in $dH_2O$ for 24 h (Control for CaP-SM 1).
- SM2: Lyophilised SM1 scaffolds immersed in $dH_2O$ for 48 h (Control for CaP-SM 2).
- CaP-SM1: Smart Matrix® scaffolds immersed in SBF-1 for 24 h. CaP mineral deposits present a globular morphology.
- CaP-SM2: Lyophilised SmartCaP1 scaffolds further immersed in SBF-3 for 48 h. CaP mineral deposits present a plate-like morphology.

EXAMPLE 4

Methods & Results for Testing the Alternative Scaffolds a) Scanning Electron Microscopy (SEM) and Energy Dispersive X-ray Spectroscopy (EDX)

Results in FIG. 10 show CaP mineral deposits with a globular morphology distributed evenly throughout the fibrin matrix in CaP-SM1. A plate-like morphology is observed in CaP-SM2. SM1 and SM2 show the typical fibres seen in Smart Matrix®.

EDX elemental analysis (FIG. 11) showed that the main elements in the mineral deposits of CaP-SM1 and CaP-SM2 were Ca and P. Calculated Ca/P was 1.29±0.28 and 1.02±0.37 (average±standard deviation) for CaP-SM1 and CaP-SM2, respectively. Mg was also present in CaP-SM1 spectra.

b) Fourier Transform Infrared Spectroscopy (FTIR) and X-Ray Diffraction (XRD)

Analysis of functional groups in the CaP deposits was carried out by FTIR. Spectra were obtained by placing the scaffolds in contact with Attenuated Total Reflectance accessory (Golden Gate ATR, Specac, UK). Spectrum software v 5.0.1 (Perkin-Elmer, UK) identified the peak intensities of each chemical group (the wavenumber was fixed between 500-4000 $cm^{-1}$ with a resolution of 4 $cm^{-1}$).

Phase composition and crystallinity of the CaP deposits were studied by XRD using a RIGAKU D/max 2500 Diffractometer operated at 40 kV and 80 mA with graphite-filtered Cu Kα radiation. Data was collected from 2θ=5° to 80° with a step size of 0.03°.

FTIR spectra displayed in FIG. 12 show that differences exist between the controls (SM1 and SM2) and the CaP-SM scaffolds. $PO_4$ burst peaks can be seen for the CaP-SM samples at approximately 1050 $cm^{-3}$ followed by a small shoulder peak at approximately 850 $cm^{-1}$ which could be due to a $HPO_4$ group or a $CO_3$ group or both. A peak at approximately 600 $cm^{-1}$, specially visible for CaP-SM2, could be due to a $PO_4$ group. The small peak seen at approximately 1450 $cm^{-1}$ for CaP-SM1 could be due to a $CO_3$ group. Moreover, spectra show that $PO_4$ peaks grow in intensity in CaP-SM2 compared to CaP-SM1 suggesting deposition of a higher amount of a phosphate mineral phase in CaP-SM2 than in CaP-SM1 scaffolds. FTIR results suggest the presence of $PO_4$, and possibly both $HPO_4$ and $CO_3$ groups, especially in CaP-SM1, in the CaP deposits.

XRD spectra of CaP-SM1 did not show peaks as the CaP deposits in these scaffolds are very amorphous and XRD does not detect very amorphous mineral phases. For CaP-SM2 XRD spectra revealed peaks that could correspond to hydroxyapatite (HA) and/or octacalcium phosphate (OCP). However, these peaks were broad indicating the CaP mineral phase/s present in CaP-SM2 were not very crystalline. Taking into account that the Ca/P ratio calculated by EDX is approximately 1, CaP-SM2 could be composed of a combination of CaP phases, for example OCP and amorphous calcium phosphate (ACP): Ca/P=1.33 and Ca/P=0.67-1.5 for OCP and ACP, respectively (Habraken et al. 2016).

c) Von Kossa Staining of Cross-Sections

FIG. 13 shows Von Kassa stained scaffolds counterstained with eosin. Although it may not readily be visible from FIG. 13, CaP mineral deposits are stained black/dark brown while the fibrin fibres stain pink/red. As observed from FIG. 13, CaP mineral deposits are found throughout the scaffold structure suggesting an even deposition of CaP throughout the scaffolds. No CaP mineral deposits were observed on the SM1 and SM2 control samples.

d) Rheology

Rheology is a branch of engineering that studies the viscoelastic properties (both solid and fluid) of materials as well as biological tissues (Holt et al. 2008; Saitoh et al. 2010). A Kinexus Rheometer (Malvern Instruments, UK) in an oscillatory mode was used. From each scaffold 2 cm×2 cm samples were prepared and placed between two 20 mm diameter parallel plates (gap between plates=0.3 mm). The sample was hydrated and an integrated temperature controller was used to maintain the temperature of the sample stage at 20° C. A combined measurement including an 'amplitude sweep' and a 'frequency sweep' was carried out on each sample. The 'amplitude sweep' was performed by applying controlled stresses that were linearly increased from 0.05 to 5%. Strains corresponding to the stresses were recorded. The oscillatory frequency was maintained at 1 Hz. The maximum strain within the linear viscoelastic region (LVER) was chosen from the 'amplitude sweep'. The shear or storage modulus G' was calculated for the different samples. G' is related to elasticity and is an indication of how the material stores energy which can be re-used in the form of elastic deformation. Thus, G' relates to the solid characteristics of the material.

Calculated G' for the different scaffolds (as mean±standard error mean) was 11.24±2.54 kPa for SM1, 11.04±2.33 kPa for SM2, 75.22±55.40 kPa for CaP-SM1 and 561.33±109.79 kPa for CaP-SM2. Therefore, adding a CaP mineral phase to the fibrin-based matrix strengthens the material. A plate-like morphology makes the scaffold stronger than a globular morphology.

e) In Vitro Bio-Degradability (Trypsin Digestion)

Scaffolds (Smart Matrix®, demineralised bone matrix or DBM, CaP-SM 1 and CaP-SM 2) were cut into 5 mm×5 mm square pieces prior to treatment with 1% trypsin at pH 7.2 at 37° C. for up to 48 h hours. Scaffolds were immersed in PBS alone as controls. Samples were imaged macroscopically using canon camera and microscopically using a stereomicroscope at 0 h, 18 h, 24 h and 48 h.

Images in FIG. 14 show that after 48 h both Smart Matrix® and DBM are completely degraded while pieces of CaP-SM 1 and CaP-SM 2 are still visible. CaP-SM 1 degraded to a greater extent than CaP-SM 2 after 48 h in 1% Trypsin. These results suggest that CaP-SM scaffolds would take longer to degrade in vivo than Smart Matrix® or DBM.

f) Cell Viability and Proliferation by Live/Dead and AlarmarBlue® Assays

Scaffolds (Smart Matrix® used as control, CaP-SM 1 and CaP-SM 2) were cut into 5 mm×5 mm square pieces and sterilised with 70% IMS, washed three times with PBS and placed in flat bottomed-24 well ultra-low attachment plates. The scaffolds were seeded with 1×10 MC3T3-E1 subclone mouse pre-osteoblasts (osteoprogenitor cells) in 20 µl medium. After seeding, the plates were incubated for 3 h at 37° C. with 5% $CO_2$ to allow cells to attach to the scaffolds. After the attachment incubation time, 1 ml of αMEM (*Minimum Essential Medium Eagle Alpha Modification* with 1% antibiotics and 10% fetal calf serum) with (+OM) or without (−OM) osteogenic supplements (50 µg/ml ascorbic acid, 10 mM β-glycerophosphate and 100 nM dexamethasone) was added per well and cultured over a 28 day period at 37° C. with 5% $CO_2$.

Seeded scaffolds were assessed for cell incorporation and viability using Live/Dead cell staining according to the manufacturer's guidelines (Sigma), wherein live cells fluoresce green and dead cells fluoresce red. Briefly, scaffolds were washed in PBS prior to staining with the live/dead staining solution and then the staining procedure was performed in the dark for 30 min at 37° C. and 5% $CO_2$. Live and dead cells were visualized by fluorescence imaging and confocal microscopy.

Seeded scaffolds were transferred to fresh 24 well plates and 1 ml of alamarBlue® working solution (diluted 10× from stock solution with phenol free Dubelcco's Modified Eagles Medium supplemented with 10% FCS and 1% antibiotics) was added per well and samples incubated at 37° C. with 5% $CO_2$ for 3 h, after which each well content was transferred to a cuvette and absorbance measured at 570 nm in a uv/vis spectrophotometer.

Results showed that cells remained viable over the culture period and were able to proliferate. The Live/Dead assay showed green fluorescent cells (viable) on all scaffolds both under standard and osteogenic conditions (FIG. 15). Images also show that cells grow in clusters in CaP-SM scaffolds compared to Smart Matrix®. Cells seemed to initially proliferate faster in Smart Matrix® control and CaP-SM1 scaffolds until reaching a plateau at day 14 while in CaP-SM 2 cells did not reach a plateau in growth over the culture period (FIG. 16). These results suggest that CaP-SM 1 and CaP-SM 2 keep the beneficial cellular properties of Smart Matrix®.

g) Cell Migration through the CaP-SM

Seeded CaP-SM scaffolds after 28 days of culture were fixed in 4% paraformaldehyde, processed for paraffin histology and stained with standard Haematoxylin & Eosin (H&E) as in Example 1.

Images in FIG. 17 show that MC3T3-E.1 cells were able to migrate through the CaP-SM scaffolds and after 28 days of culture populated the scaffolds throughout. Smart Matrix has been shown to promote influx and migration of cells both in vitro and in vivo (Garcia-Gareta et al. 2013; Sharma et al. 2016) and these results show that CaP-SM scaffolds retain this property.

Additionally, distribution of MC3T3-E1 cells within Smart Matrix®, CaP-SM 1 and CaP-SM2 scaffolds was examined using DAPI staining of the nuclei after 28 days of culture under standard (−OM) and osteogenic (+OM) conditions. Histological slides were deparaffinised, rehydrated and washed in distilled water before Fluoroshield™ with DAPI mounting media (F6057 Sigma) was applied as per manufacturer's instructions. Briefly, the vial was brought to room temperature and 1-2 drops of the mounting media was applied directly on top of the sample and left to set for approximately 5 minutes at room temperature. The sections were then cover slipped carefully avoiding air bubbles and the edges were sealed using a nail varnish. The sections were then imaged using confocal scanning laser microscope using 405 nm wavelength laser for DAPI (Excitation 372, Emission 456). The sections were tile scanned for the entire XY plane of the scaffold and then merged using 5% overlap automated function of the confocal microscope.

Images in FIG. 18 show that cells populate the scaffolds throughout and are evenly distributed through the depth of the scaffolds.

h) Cell Integration

After 28 days in culture either under standard or osteogenic conditions, seeded scaffolds were fixed with 2.5% glutaraldehyde. Prior to and post-fixing in 1% osmium tetraoxide (Sigma-Aldrich) for 1 h, the samples were washed in 0.1 M sodium cacodylate buffer. This was followed by dehydration of samples through a graded series of IMS (20%-60%) and ethanol (70%-100%). Samples were left in 100% ethanol and the ethanol was allowed to evaporate overnight. Dried cellularised and acellular samples were mounted on stubs, carbon coated (Agar Auto Sputter Coater, Agar Scientific) and viewed under the SEM microscope (FEI Inspect F, Oxford Instruments, Oxford, UK).

Results showed cells integrated with the CaP-SM scaffolds in both standard and osteogenic culture conditions (FIG. 19). Cells can be seen forming a layer of interconnected cells which in some areas is embedded within the scaffolds. Some cytoplasmic processes are seen on all samples. These results demonstrate the good cellular properties of CaP-SM scaffolds.

i) Osteogenic Differentiation

Scaffolds (Smart Matrix® used as control, CaP-SM 1 and CaP-SM 2) were cut into 5 mm×5 mm square pieces, sterilised, seeded with 1×10 MC3T3-E1 and cultured in both standard and osteogenic media as already explained.

Deposition of non-collagenous matrix was assessed by osteopontin immunostaining of paraffin embedded sections. Briefly, antigen retrieval was performed by heat mediated antigen retrieval using sodium citrate buffer at pH 6. After antigen retrieval the sections were blocked using 5% bovine serum albumin at 35° C. for 1 h and stained with primary anti-osteopontin antibody (1:50, abcam ab8448) at 4° C. overnight. Following this, the sections were stained using the alexa fluor 546 secondary antibody for 2 h at room temperature. The sections were then washed and mounted with DAPI based mounting media, cover slipped and visualised using Leica DM IRE2 confocal microscope.

Mineralisation was assessed by Von Kossa staining as already explained.

Immunostaining of osteopontin, a protein present in the extracellular matrix of bone, showed that MC3T3-E1 differentiated down the osteogenic pathway in CaP-SM 1 and CaP-SM 2 scaffolds (FIG. 20, where red fluorescence indicates presence of osteopontin; although this may not be readily observed in black and white versions of the figure). Greater differentiation was observed in samples cultured under osteogenic conditions as expected. Von Kossa staining showed extensive mineral deposition in CaP-SM seeded scaffolds in comparison to the Smart Matrix® control (FIG. 21).

These results show that the CaP mineral deposits present in the CaP-SM scaffolds promote differentiation of osteoprogenitor cells down the osteogenic pathway.

j) Angiogenesis

Proangiogenic; potential of the scaffolds was assessed using an ex ovo chorionic allantoic membrane (CAM) assay. Scaffolds (Smart Matrix® used as control, CaP-SM 1 and CaP-SM 2) were cut into 5 mm×5 mm square pieces, sterilised with 70% IMS and washed three times with PBS. A negative and a positive control were run alongside the scaffolds: filter paper soaked in either PBS (negative) or 10 ng/ml of vascular endothelial growth factor (VEGF) solution (positive). Fertile chicken eggs were incubated at 37.5° C., 3% $CO_2$ and humidity was maintained between 35%-45%. At day 3 post-incubation, the embryos were transferred to a shell-less culture system with 75-80% humidity and 37.5° C. incubation temperature. At day 6 of shell-less culture time, scaffolds were applied onto the developing CAMs. Angiogenesis was examined in all the scaffolds macroscopically by taking photos using a stereomicroscope. ImageJ software was used to analyse the macroscopic photos and calculate the percentage of vascular area for each scaffold.

Results from the CAM assay (FIG. 22) showed that CaP-SM 1 and CaP-SM 2 scaffolds had very similar pro-angiogenic potential to Smart Matrix® scaffolds. Smart Matrix® has been shown to be pro-angiogenic in vivo, therefore results suggest that CaP-SM 1 and CaP-SM 2 scaffolds would retain this pro-angiogenic potential after addition of a CaP mineral phase. REFERENCES Ahmed T A E, Dare E V, Hincke M. (2008) Fibrin: A versatile scaffold for tissue engineering applications. *Tissue Eng Part B* 14(2), 199-215.

Cui G, Li J, Lei W, Bi L, Tang P, Liang Y, Tao S, Wang Y, (2010) The mechanical and biological properties of an injectable calcium phosphate cement-fibrin glue composite for bone regeneration. *J Biomed Mater Res B Appl Biomater* 92(2), 377-85.

Dong J, Cui G, Bi L, Li J, Lei W. (2013) The mechanical and biological studies of calcium phosphate cement-fibrin glue for bone reconstruction of rabbit femoral defects. *Int J Nanomedicine* 8, 1317-24.

Garcia-Gareta E, Hua J, Knowles J C, Blunn G W. (2013) Comparison of mesenchymal stem cell proliferation and differentiation between biomimetic and electrochemical coatings on different topographic surfaces. *J Mater Sci Mater Med* 24(1), 199-210.

Garcia-Gareta E, Coathup M J, Blunn G W. (2015) Osteoinduction of bone grafting materials for bone repair and regeneration. *Bone* 81, 112-121.

Garcia-Gareta E, Ravindran N, Sharma V, Samizadeh S, Dye J F. (2013) A novel multiparameter of in vitro model of three-dimensional cell ingress into scaffolds for dermal reconstruction to predict in vivo outcome. *Biores Open Access* 2(6), 412-420.

Hadjidakis D J, Androulakis II. (2006) Bone remodelling. *Ann NY Acad Sci* 1092, 385-396. Ignjatovic N, Ajdukovic Z, Uskokovic D. (2005) New biocomposite [biphasic calcium phosphate/poly-DL-lactide-co-glycolide/biostimulative agent] filler for reconstruction of bone tissue changed by osteoporosis. *J Biomed Sci Mater Med* 16(7), 621-6.

Habraken W, P, Epple M, Bohner M. (2016) Calcium phosphates in biomedical applications: materials for the future? *Mater Today* 19(2):69-87.

Holt B, Tripathi A, Morgan J. (2008) Viscoelastic response of human skin to low magnitude physiologically relevant shear. *J Biomech* 41(12):2689-95.

Kokubo T, Kushitani H, Sakka S, Kitsugi T, Yamamuro T. (1990) Solutions able to reproduce in vivo surface-structure changes in bioactive glass-ceramic A-W. *J biomed Mater Res* 24, 721-734.

LeGeros R Z. (2008) Calcium phosphate-based osteoinductive materials. *Chem Rev* 108, 4742-4753.

Lopez-Heredia M A, Pattipeilohy J, Hsu S, Grykien M, van der Weijden B, Leeuwenburgh S C, Salmon P, Wolke J G, Jansen J A. (2013) Bulk physicochemical, interconnectivity, and mechanical properties of calcium phosphate cements-fibrin glue composites for bone substitute applications. *J Biomed Mater Res A* 101(2), 478-90.

Mishra R, Roux B M, Posukonis M, Bodamer E, Brey E M, Fisher J P, Dean D. (2016) Effect of prevascularization on in vivo vascularization of poly(propylene fumarate)/fibrin scaffolds. *Biomaterials* 77, 255-66.

Perez R A, Kim M, Kim T H, Kim J H, Ho Lee J, Park J H, Knowles J C, Kim H W. (2014) Utilizing core-shell fibrous collagen-alginate hydrogel cell delivery system for bone tissue engineering. *Tissue Eng Part A* 20, 103-114.

Qian G, Dong Y, Yang W, Wang M. (2012) Injectable calcium phosphate cement and fibrin sealant recombined human bone morphogenetic protein-2 composite in vertebroplasty: an animal study. *Bosn J Basic Med Sd* 12(4), 231-5.

Saitoh S, Sasaki K, Nezu T, Taira M. (2010) Viscoelastic behaviour of commercially available tissue conditioners under compression. *Dent Mater J* 29(4):461-468.

Sharma V, Patel N, Kohli N, Ravindran N, Hook L, Mason C, Garcia-Gareta E. (2016) Viscoelastic, physical, and bio-degradable properties of dermal scaffolds and related cell behaviour. *Biomed Mater* 11:055001.

Sharma V, Blackwood K A, Haddow D, Hook L, Mason C, Dye J F, Garcia-Gareta E. (2015) Method for estimating protein binding capacity of polymeric systems. *Biochimie Open* 1, 40-50.

V. Sharma, N. Patel, J. F. Dye, L. Hook, C. Mason, E. Garcia-Gareta, Albumin removal from human fibrinogen preparations for manufacturing human fibrin-based biomaterials, Biochimie. Open. 1 (2015) 6-10

Wopenka B, Pasteris J D. (2005) A mineralogical perspective on the apatite in bone. *Mater Sci Eng C* 25, 131-143.

Xiu J, Fan J, Li J, Cui G, Lei W. (2014) Different angiogenic abilities of self-setting calcium phosphate cement scaffolds consisting of different proportions of fibrin glue. *Biomed Res Int* 2014:785146.

The invention claimed is:

1. An extracellular matrix material, comprising:
   a cross-linked scaffold comprising fibrin or fibrinogen, and a bulking agent, wherein the fibrin or fibrinogen and the bulking agent are covalently cross-linked, and the bulking agent is covalently cross-linked to the fibrin or fibrinogen; and
   a ceramic deposited on the scaffold.

2. An extracellular matrix according to claim 1, wherein the ceramic is, or comprises, a calcium phosphate mineral phase.

3. An extracellular matrix material according to claim 1, wherein the bulking agent is an alginate, a glycosaminoglycan, hydroxyethylstarch, ethyl cellulose, Xanthan gum, or agarose.

4. A process for preparing an extracellular matrix material, comprising:
   depositing a ceramic on a cross-linked scaffold comprising fibrin or fibrinogen, and a bulking agent, wherein the fibrin or fibrinogen and the bulking agent are covalently cross-linked, and the bulking agent is covalently cross-linked to the fibrin or fibrinogen.

5. A process according to claim 4, wherein the ceramic is a calcium phosphate mineral phase.

6. A process according to claim 4, wherein the calcium phosphate mineral phase is deposited on the scaffold by biomimetic deposition.

7. A process according to claim 4, wherein the calcium phosphate mineral phase is deposited on to the scaffold by immersing the scaffold in a fluid comprising
   i) $Ca^{2+}$ and $HPO_4^{2-}$;
   ii) $Ca^{2+}$, $HPO_4^2$, $Na^+$, $K^+$, $Mg^{2+}$, $Ca^{2+}$, $Cl^-$, $HCO_3^-$, $HPO_4^{2-}$, $HPO_4^{2-}$ and $SO_4^{2-}$;
   iii) $Ca^{2+}$, $HPO_4^2$, $Na^+$, $K^+$, $Mg^{2+}$, $Ca^{2+}$, $Cl^-$, $HCO_3^-$, and $HPO_4^{2-}$; or
   iv) $Ca^{2+}$, $HPO_4^2$, $Na^+$, and $K^+$.

8. A process as defined in claim 5, wherein the calcium phosphate mineral phase is deposited on to the scaffold by contacting the scaffold with, or immersing the scaffold in, a fluid comprising one or more of:
   a) 1 to 30 mM $Ca^{2+}$;
   b) 0.5 to 10 mM $HPO_4^{2-}$;
   c) 100 to 800 mM $Na^+$;
   d) 1 to 50 mM $K^+$;
   e) 0.5 to 20 mM $Mg^{2+}$;
   f) 100 to 800 mM $Cl^-$;
   g) 1 to 100 mM $HCO_3^-$; and
   h) 1 to 10 mM $SO_4^{2-}$.

9. A process according to claim 7, wherein the scaffold is contacted with, or immersed in, the fluid for at least 12 hours, at least 24 hours, at least 2 days, at least 5 days, at least 6 days, or at least 9 days.

10. A process according to claim 7, wherein the scaffold is contacted with, or immersed in the fluid for up to 20 days.

11. A process according to claim 4, comprising generating the scaffold by:
    (a) mixing an aqueous solution of fibrinogen with a coagulating agent and a bulking agent;
    (b) incubating the mixture obtained in step (a) with a cross-linking agent; and
    (c) washing the cross-linked composition obtained in step (b) to remove the cross-linking agent.

12. A process according to claim 4, comprising forming the scaffold by a process comprising the following steps:
    (a) mixing an aqueous solution of fibrinogen with a coagulating agent and a bulking agent;
    (b) incubating the mixture obtained in step (a) with a cross-linking agent; and
    (c) washing the cross-linked composition obtained in step (b) to remove the cross-linking agent.

13. A process as defined in claim 11, wherein the coagulating agent comprises an enzymatic or non-enzymatic coagulating agent.

14. A process as defined in claim 11, wherein step (a) comprises mixing with a foaming agent.

15. A process according to claim 14, wherein the foaming agent comprises a non-ionic detergent, a thermosensitive gelling surfactant, a diphosphatydylglycerol type phospholipid, a mixture of an immiscible phase with the aqueous fibrinogen solution phase, a surfactant, or a sugar-acyl surfactant.

16. A process according to claim 15, wherein the foaming agent sugar-acyl surfactants are selected from the class of pyranoside, maltoside, and acyl-sucrose surfactants.

17. A process according to claim 15, wherein the sugar-acyl surfactants are selected from the group consisting of OGP, ODM, DGP and DdGP, TGP, HGP, DMP, decyl sucrose (nDS), dodecylsucrose (nDdS), OGM, and DMP and DdGP.

18. A process according to claim 11, wherein the cross-linking agent used in step (b) is selected from: carbodiimide coupling agents, azide coupling agents; diisocyanate cross-linking agents; epoxide cross-linking agents; and aldehyde cross-linking agents.

19. A process according to claim 11 for preparing an extracellular matrix composition having a predetermined shape, wherein either (i) the mixture of step (a) is cast in a mould of a predetermined shape, frozen and optionally lyophilised prior to the incubation step (c), or; (ii) the product of step (d) is produced in a mould of a predetermined shape, and the product is then frozen and optionally lyophilised.

20. A method of bone regeneration, the method comprising application of an extracellular matrix material as defined in claim 1 to a bone defect.

21. The method of claim 20, wherein the bone is in vitro, ex vivo or in vivo.

22. An extracellular matrix material according to claim 1, which is lyophilized.

* * * * *